(12) United States Patent
Mehrabian et al.

(10) Patent No.: US 7,241,571 B2
(45) Date of Patent: Jul. 10, 2007

(54) IDENTIFICATION OF 5-LIPOXYGENASE AS A MAJOR GENE CONTRIBUTING TO ATHEROSCLEROSIS

(75) Inventors: Margarete Mehrabian, Sherman Oaks, CA (US); Aldons J. Lusis, Los Angeles, CA (US); Hooman Allayee, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 275 days.

(21) Appl. No.: 10/741,292

(22) Filed: Dec. 19, 2003

(65) Prior Publication Data

US 2004/0209288 A1   Oct. 21, 2004

Related U.S. Application Data

(63) Continuation-in-part of application No. PCT/US02/34208, filed on Oct. 24, 2002.

(60) Provisional application No. 60/335,244, filed on Oct. 24, 2001.

(51) Int. Cl.
  *C12Q 1/68* (2006.01)
  *C12P 19/34* (2006.01)
  *C07H 21/02* (2006.01)
  *C07H 21/04* (2006.01)
  *G01N 33/00* (2006.01)
  *A61K 31/70* (2006.01)
  *A61K 38/00* (2006.01)
  *A01N 37/18* (2006.01)

(52) U.S. Cl. .................. 435/6; 435/91.1; 435/91.2; 536/23.1; 536/24.3

(58) Field of Classification Search .......... None
  See application file for complete search history.

(56) References Cited

U.S. PATENT DOCUMENTS 5,428,048 A    6/1995   Malamas
6,582,957 B1 *  6/2003   Turner et al. ............... 435/325

FOREIGN PATENT DOCUMENTS

EP    0 384 594      8/1990
EP    0 745 600 A1   12/1996
WO    WO 92/03130    5/1992
WO    WO 96/12703    5/1996
WO    WO 01/70130    9/2001

OTHER PUBLICATIONS

In et al; J. Clin. Invest. vol. 99, pp. 1130-1137; 1997.*
Zhao et al; Trends in Cardiovascular Medicine, vol. 14, pp. 191-195, 2004.*
Dishart et al; Biochemica et Biophysica Acta, vol. 1738, pp. 37-47, 2005.*
Dixon et al., Cloning of the CDNA for Human 5-Lipoxygenase, Biochemical (1988), *Proc. Natl. Acad. Sci.*, 85: 416-42.
Drazen et al., Pharmacogentic Association Between ALOX5 Promoter Genotype and the Response to Anti-Asthma Treatment, (1999), *Nature Genetics*, 22:168-170.
In et al., Naturally Occuring Mutations in the Human 5-Lipoxygenase Gene Promoter That Modify Transcription Factor Binding and Reporter Gene Transcription, (1997), *J. Clin. Invest.*, 99:1130-1137.
Lusis, Atherosclerosis, (2000,) *Nature*, 407:233-41.
Mehrabian et al., Genetic Locus in Mice That Blocks Development of Atherosclerosis Despite Extreme Hyperlipidemia, (2001), *Circ Res*, 89:125-30.
Mehrabian et al., Identification of 5-Lipoxygenase as a Major Gene Contributing to Atherosclerosis susceptibility in Mice, Circ. Res., 2002, 91:120-126.

* cited by examiner

*Primary Examiner*—Jehanne Sitton
(74) *Attorney, Agent, or Firm*—Bozicevic, Field & Francis LLP; Pamela J. Sherwood

(57) ABSTRACT

5-LO is expressed in the monocyte/macrophages (mono/mac) and foam cells of atherosclerotic lesions and is differentially expressed in CAST and CON6 mice relative to B6 mice. Mice heterozygous for a null mutation of 5-LO, when placed on an LDLR−/− background, have dramatically reduced atherosclerosis as compared to control LDLR−/− mice. In a genetic epidemiologic study, it is found that a common 5-LO polymorphism is strongly associated with carotid artery intima-media thickness (IMT) and coronary artery disease patients. These results indicate that 5-LO and the leukotriene biosynthetic pathway is a major contributor to atherogenesis in animal models, and in atherosclerosis susceptibility in humans.

3 Claims, 12 Drawing Sheets

* $P < 0.0001$

FIGURE 3A 3D
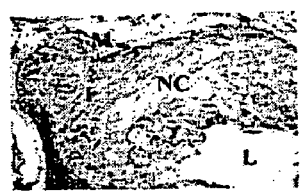
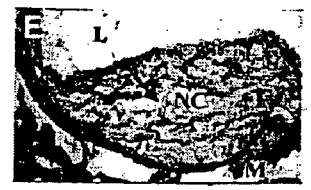
3B 3E
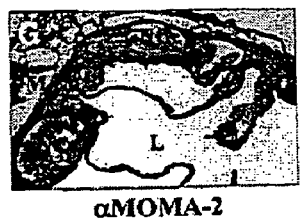
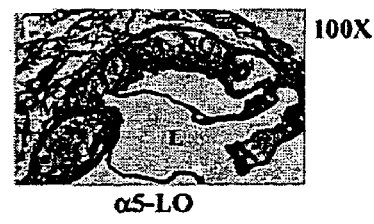
αMOMA-2 α5-LO
3C 3F FIGURE 4A        4B
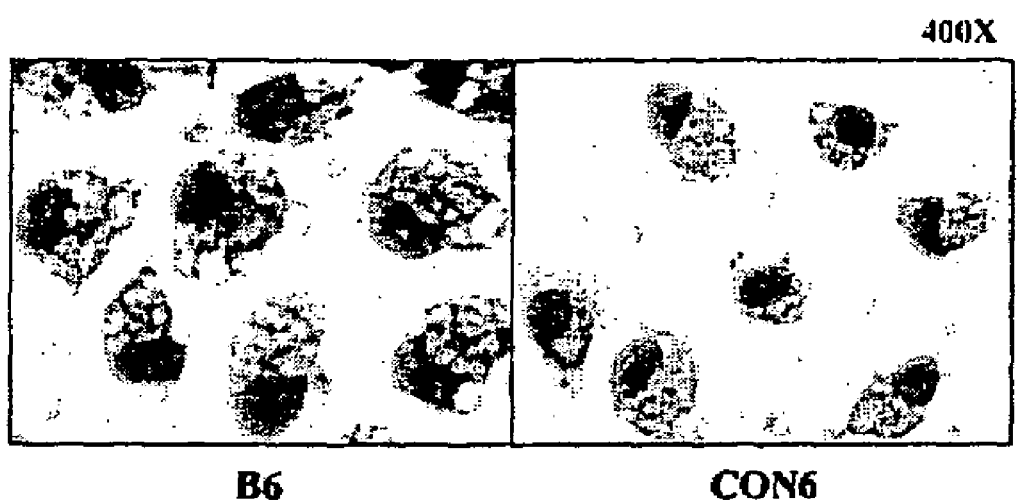

IDENTIFICATION OF 5-LIPOXYGENASE AS A MAJOR GENE CONTRIBUTING TO ATHEROSCLEROSIS

GOVERNMENT RIGHTS

This invention was supported by a grant from the American Heart Association Grant-in-Aid 0355031Y. The U.S. government may have certain rights in the invention.

INTRODUCTION

Cardiovascular disease is a major health risk throughout the industrialized world. Atherosclerosis, the most prevalent of cardiovascular diseases, is the principal cause of heart attack, stroke, and gangrene of the extremities, and thereby the principle cause of death in the United States. Atherosclerosis is a complex disease involving many cell types and molecular factors. The process, in normal circumstances, is a protective response to insults to the endothelium and smooth muscle cells (SMCs) of the wall of the artery, consists of the formation of fibrofatty and fibrous lesions or plaques, preceded and accompanied by inflammation. The advanced lesions of atherosclerosis may occlude the artery concerned, and result from an excessive inflammatory-fibroproliferative response to numerous different forms of insult. For example, shear stresses are thought to be responsible for the frequent occurrence of atherosclerotic plaques in regions of the circulatory system where turbulent blood flow occurs, such as branch points and irregular structures.

The first observable event in the formation of an atherosclerotic plaque occurs when blood-borne monocytes adhere to the vascular endothelial layer and transmigrate through to the sub-endothelial space. Adjacent endothelial cells at the same time produce oxidized low density lipoproteins (LDL). These oxidized LDL's are then taken up in large amounts by the monocytes through scavenger receptors expressed on their surfaces. In contrast to the regulated pathway by which native LDL (nLDL) is taken up by nLDL specific receptors, the scavenger pathway of uptake is not regulated by the monocytes.

These lipid-filled monocytes are called foam cells, and are the major constituent of the fatty streak. Interactions between foam cells and the endothelial and SMCs which surround them lead to a state of chronic local inflammation which can eventually lead to smooth muscle cell proliferation and migration, and the formation of a fibrous plaque. Such plaques occlude the blood vessel concerned and thus restrict the flow of blood, resulting in ischemia.

Ischemia is a condition characterized by a lack of oxygen supply in tissues of organs due to inadequate perfusion. Such inadequate perfusion can have number of natural causes, including atherosclerotic or restenotic lesions, anemia, or stroke, to name a few. Many medical interventions, such as the interruption of the flow of blood during bypass surgery, for example, also lead to ischemia. In addition to sometimes being caused by diseased cardiovascular tissue, ischemia may sometimes affect cardiovascular tissue, such as in ischemic heart disease. Ischemia may occur in any organ, however, that is suffering a lack of oxygen supply.

The most common cause of ischemia in the heart is atherosclerotic disease of epicardial coronary arteries. By reducing the lumen of these vessels, atherosclerosis causes an absolute decrease in myocardial perfusion in the basal state or limits appropriate increases in perfusion when the demand for flow is augmented. Coronary blood flow can also be limited by arterial thrombi, spasm, and, rarely, coronary emboli, as well as by ostial narrowing due to luetic aortitis. Congenital abnormalities, such as anomalous origin of the left anterior descending coronary artery from the pulmonary artery, may cause myocardial ischemia and infarction in infancy, but this cause is very rare in adults. Myocardial ischemia can also occur if myocardial oxygen demands are abnormally increased, as in severe ventricular hypertrophy due to hypertension or aortic stenosis. The latter can be present with angina that is indistinguishable from that caused by coronary atherosclerosis. A reduction in the oxygen-carrying capacity of the blood, as in extremely severe anemia or in the presence of carboxy-hemoglobin, is a rare cause of myocardial ischemia. Not infrequently, two or more causes of ischemia will coexist, such as an increase in oxygen demand due to left ventricular hypertrophy and a reduction in oxygen supply secondary to coronary atherosclerosis.

Publications.

The sequence of human 5LO is reported by Dixon et al. (1988) *Proc. Nat. Acad. Sci.* 85: 416–42. Drazen et al. (1999) *Nature Genetics* 22:168–170 report a pharmacogenetic association between 5-LO promoter genotype and the response to anti-asthma treatment, which article is herein specifically incorporated by reference. In et al. (1997) *J. Clin. Invest.* 99:1130–1137 describe naturally occurring mutations in the human 5-LO gene promoter.

Lusis (2000) *Nature* 407:233–41 reviews atherosclerosis. Mehrabian et al. (2001) *Circ Res* 89:125–30 describes the positional mapping of a locus involved in susceptibility to athersclerosis.

SUMMARY OF THE INVENTION

The present invention provides methods and compositions for the treatment and diagnosis of cardiovascular disease, including but not limited to, atherosclerosis, ischemia/reperfusion, hypertension, restenosis, and arterial inflammation; and also for the diagnosis of hyperglycemic conditions, including diabetes, insulin resistance, and the like. Specifically, the 5-lipoxygenase gene and the leukotriene biosynthetic pathway is identified as associated with a susceptibility to cardiovascular disease states. Alleles, including variations in the 5-lipoxygenase promoter region, are associated with disease susceptibility, and their detection is used in the diagnosis of a predisposition to these conditions. Similarly, genes in the leukotriene biosynthesis are also involved in susceptibility and disease diagnosis of disease.

The invention also provides methods for the identification of compounds that modulate the expression of genes or the activity of gene products involved in cardiovascular disease, as well as methods for the treatment of cardiovascular disease, which may involve the administration of such compounds to individuals exhibiting cardiovascular disease symptoms or tendencies.

A major locus for susceptibility to atherosclerosis has been identified on mouse chromosome 6. This genetic locus provides almost complete resistance to atherogenesis despite extreme hyperlipidemia resulting from a deficiency of the low density lipoprotein receptor (LDLR$^{-/-}$). The gene encoding 5-lipoxygenase (5-LO) has been mapped to this region. 5-LO is expressed in the monocyte/macrophages (mono/mac) and foam cells of atherosclerotic lesions and is differentially expressed in animals resistant to atherogenesis when compared to susceptible animals.

BRIEF DESCRIPTION OF THE DRAWINGS

FIGS. 3A–3F. 5-LO is present in atherosclerotic lesions of apoE−/− and LDLR−/− mice. A through C, Staining of aortic sections with macrophage-specific MOMA-2 showed large advanced lesions. D through F, Adjacent proximal sections stained with anti-5-LO antibody showing colocalization of 5-LO (arrow) with a subset of macrophages surrounding the necrotic core (NC) but not with all regions staining for macrophages. A and D and B and E are from two 1-year-old apoE−/− mice on a chow diet. C and F are representative of lesions from a 4- to 6-month-old LDLR−/− mouse on a high-fat, high-cholesterol diet for 8 weeks. I indicates intima; L, lumen; and M, media.

FIGS. 4A and 4B. Decreased 5-LO protein in macrophages from CON6 compared with B6 mice. Peritoneal monocyte/macrophage were isolated 3 days after thioglycolate treatment from 4- to 6-month-old CON6 (n=4) and B6 (n=4) mice on a chow diet. Cells were cultured overnight on glass slides and stained with a 5-LO-specific antibody and hematoxylin.

DETAILED DESCRIPTION OF THE EMBODIMENTS

Figure 1A:
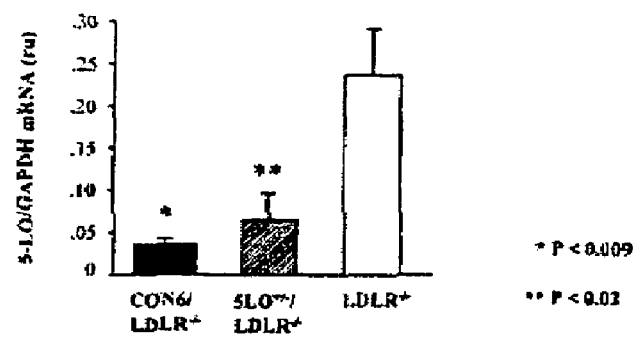
FIGS. 1A and 1B. Decreased 5-LO mRNA and protein levels in bone marrow cells from CON6 mice compared with B6 controls. A, Total bone marrow RNA was isolated from CON6/LDLR−/− (n=3), 5LO+/−/LDLR−/− (n=3), and LDLR−/− (n=3) mice, and analysis was performed using a cDNA probe to either 5-LO or GAPDH as a control. Levels of mRNA were quantitated by phosphorimaging and are expressed as the ratio of 5-LO to GAPDH. B, Immunoblot analysis of bone marrow homogenates from B6 (n=4) and CON6 (n=4) mice were performed using a specific commercially available rabbit anti-human 5-LO antibody (Cayman Chemical). Data are from 4- to 6-month-old mice on a chow diet and are representative of at least 3 experiments.

Methods and compositions for the diagnosis and treatment of cardiovascular disease, including but not limited to atherosclerosis, ischemia/reperfusion, hypertension, restenosis, and arterial inflammation, are described. The invention is based, in part, on the evaluation of the expression and role of 5-LO, which is both differentially expressed in disease models, and for which alleles predisposing to atherogenesis are herein identified. This permits the definition of disease pathways and the identification of a target in the pathway that is useful both diagnostically, in drug screening, and therapeutically. Alleles of 5-LO that predispose to coronary artery disease (CAD) are also associated with insulin resistance and may be indicative of a predisposition to diabetes.

The leukotrienes constitute a group of arachidonic acid-derived compounds with biologic activities suggesting important roles in inflammation and immediate hypersensitivity. The enzyme 5-lipoxygenase (EC 1.13.11.34) catalyzes 2 reactions in the formation of leukotrienes. Matsumoto et al. (1988) *Proc. Nat. Acad. Sci.* 85:26–30 herein incorporated by reference, isolated cDNA clones for human lung and placenta 5-lipoxygenase and deduced the complete amino acid sequence of the enzyme.

Alleles of the human 5-LO gene have a promoter polymorphism, in which there is a variable number of tandem binding sites for the transcription factors Sp1/Egr-1 (Drazen et al. (1999) *Nat Genet* 22:168–70; and In et al. (1997) *J.*

Clin. Invest. 99:1130–1137, herein incorporated by reference), where each repeat has the sequence motif GGGCGG. The common allele in the human population consists of five repeated binding sites and has been termed the "5", or "N" allele. Alleles with less than 5 repeats, usually 3 repeats or 4 repeats, may be referred to numerically as "3" or "4", or collectively as deleted, or "D" alleles. Alleles with expanded repeats greater than 5 in number, usually 6 or 7 repeats, may be referred to collectively as "E" expanded or "A" addition alleles. Four genotypic groups have been defined: homozygous 55 (indicating that both alleles consisted of five repeated binding sites); 33, 34, and 44 (one or two binding sites deleted); 35 and 45 (one allele deleted); and 56, 57, and 67 (one or both alleles expanded). A comparison between the genotypic groups revealed that individuals carrying deleted repeat alleles (genotypes 33, 34, or 44) had greatly increased incidence of coronary artery disease compared to individuals with either wild type alleles or larger numbers of repeats.

Predisposing 5-LO allele can have one or more Sp1/Egr-1 binding sites deleted, usually at least one binding site deletion on each chromosome, relative to the common allele in the human population, which wild type allele consists of five repeated Sp1/Egr-1 binding sites. Typically such susceptible alleles will have not more than 4 Sp1/Egr-1 binding site repeats. Other predisposing alleles are those changes in the 5-LO DNA sequence that confer an increased susceptibility to atherosclerosis.

In addition to 5-LO, other members of the metabolic pathway leading to the biosynthesis of leukotrienes may be involved in susceptibility to cardiovascular disease. This pathway involves several enzymes and consists of two main branches. Upon activation of the cell by calcium, arachidonic acid is released from the nuclear membrane by cytosolic phospholipase A2 (cPLA2). 5-lipoxygenase activating protein (FLAP) then presents the fatty acid to 5-LO, which subsequently catalyzes the rate-limiting step of LT synthesis by incorporating molecular oxygen into arachidonic acid and generating LTA4. LTA4 can then be converted to LTB4 via LTA4 hydrolase (LTA4H) or shunted into the cysteinyl leukotriene pathway and converted to LTC4 by LTC4 synthase (LTC4S), which is then converted to LTD4 and subsequently LTE4 by g-glutamyl transferase and LTD4 peptidase, respectively. LTB4 binds to cell surface receptors known as LTB4 receptor 1 (LTB4R1) or LTB4 receptor 2 (LTB4R2) and the cysteinyl leukotrienes (LTC4, LTD4, and LTE4) bind to their respective receptors, CysLTR1 and CysLTR2. As a result, these molecules stimulate proinflammatory signaling pathways in target cells. Thus, the identification of the entire LT synthesis pathway and all the genes involved in this metabolic process are considered as having effects on atherosclerosis development. Genetic variations in other genes of the pathway, including but not limited to, cPLA2, FLAP, LTA4H, LTC4S, LTB4R1, LTB4R2, CysLTR1, and CysLTR2 can be associated with and causal in atherosclerosis. Similar to susceptibility alleles that have been identified in 5-LO, alleles of other pathways genes can exist in human populations that similarly increase atherosclerosis and the incidence of myocardial infarction.

In one aspect of the present invention, methods are provided for determining a predisposition to atherosclerosis in an individual. The methods comprise an analysis of genomic DNA in an individual for an allele of the 5-lipoxygenase promoter, which confers an increased susceptibility to atherosclerosis. Individuals are screened by analyzing their genomic 5-LO gene sequence for the presence of a predisposing allele, as compared to a normal 5-LO sequence. The normal 5-LO sequence shall be understood to include sequence variants in non-coding regions that do not affect the level of expression of the gene, and coding region variants that do not change the amino acid sequence, e.g. "third position" changes. The methods also comprise the analysis of genomic DNA in an individual for other leukotriene synthesis genes, which can also confer increased risk for atherosclerosis.

The effect of a sequence variation on 5-LO expression or function can be determined by analysis for segregation of the sequence variation with the disease phenotype, e.g. incidence of CAD, presence of glucose tolerance, insulin levels, etc. A predisposing mutation will segregate with incidence of the disease. As an alternative to kindred studies, biochemical studies are performed to determine whether a candidate sequence variation in the 5-LO coding region or control regions affects the quantity or function of the protein. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as β-galactosidase, chloramphenical acetyltransferase, etc. that provides for convenient quantitation; and the like.

A number of methods are used for determining the presence of a predisposing mutation in an individual. Genomic DNA is isolated from the individual or individuals that are to be tested. DNA can be isolated from any nucleated cellular source such as blood, hair shafts, saliva, mucous, biopsy, feces, etc. Methods using PCR amplification can be performed on the DNA from a single cell, although it is convenient to use at least about $10^5$ cells. Where large amounts of DNA are available, the genomic DNA is used directly. Alternatively, the region of interest is cloned into a suitable vector and grown in sufficient quantity for analysis, or amplified by conventional techniques. Of particular interest is the use of the polymerase chain reaction (PCR) to amplify the DNA that lies between two specific primers. The use of the polymerase chain reaction is described in Saiki et al. (1985) *Science* 239:487, and a review of current techniques may be found in McPherson et al. (2000) PCR (Basics: From Background to Bench) Springer Verlag; ISBN: 0387916008. A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Primer pairs are selected from the 5-LO genomic sequence using conventional criteria for selection. The primers in a pair will hybridize to opposite strands, and will collectively flank the region of interest. The primers will hybridize to the complementary sequence under stringent conditions, and will generally be at least about 16 nt in length, and may be 20, 25 or 30 nucleotides in length. The primers will be selected to amplify the specific region of the 5-LO gene suspected of containing the predisposing mutation. Typically the length of the amplified fragment will be selected so as to allow discrimination between repeats of 3 to 7 units. Multiplex amplification may be performed in which several sets of primers are combined in the same reaction tube, in order to analyze multiple exons simultaneously. Each primer may be conjugated to a different label.

A diagnostic screening method of particular interest detects the number of SP-1 repeats in the promoter region of the human 5-LO gene. The organization of the region comprises a repeat region of from about 3 to about 7 6 base pair repeats of the binding motif GGGCGG, flanked by unique sequences. Within the 5' and 3' flanking sequences, sequences are selected for amplification primers. The exact composition of the primer sequences are not critical to the invention, but they must hybridize to the flanking sequences under stringent conditions. Criteria for selection of amplification primers are as previously discussed. To maximize the resolution of size differences at the locus, it is preferable to chose a primer sequence that is close to the repeat sequence, such that the total amplification product is at least about 30, more usually at least about 50, preferably at least about 100 or 200 nucleotides in length, which will vary with the number of repeats that are present, to not more than about 500 nucleotides in length. The number of repeats has been found to be polymorphic, as previously described, thereby generating individual differences in the length of DNA that lies between the amplification primers.

The primers are used to amplify the region of genomic DNA that contains the repeats. Conveniently, a detectable label will be included in the amplification reaction, as previously described. Multiplex amplification may be performed in which several sets of primers are combined in the same reaction tube. This is particularly advantageous when limited amounts of sample DNA are available for analysis. Conveniently, each of the sets of primers is labeled with a different fluorochrome.

After amplification, the products are size fractionated. Fractionation may be performed by gel electrophoresis, particularly denaturing acrylamide or agarose gels. A convenient system uses denaturing polyacrylamide gels in combination with an automated DNA sequencer, see Hunkapillar et al. (1991) Science 254:59–74. The automated sequencer is particularly useful with multiplex amplification or pooled products of separate PCR reactions. Capillary electrophoresis may also be used for fractionation. A review of capillary electrophoresis may be found in Landers, et al. (1993) BioTechniques 14:98–111. The size of the amplification product is proportional to the number of repeats (n) that are present at the locus specified by the primers. The size will be polymorphic in the population, and is therefore an allelic marker for that locus.

The amplified or cloned fragment may be sequenced by dideoxy or other methods, and the length of the amplified region, or the sequence of bases, is compared to the normal 5-LO sequence. Alternatively, where the predisposing mutation creates or destroys a recognition site for a restriction endonuclease, the fragment is digested with that endonuclease, and the products size fractionated to determine whether the fragment was digested. Fractionation is performed by gel electrophoresis, particularly acrylamide or agarose gels. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices is used to detect conformational changes created by DNA sequence variation as alterations in electrophoretic mobility. The hybridization pattern of a control and variant sequence to an array of oligonucleotide probes immobilised on a microarray, may also be used as a means of detecting the presence of variant sequences.

The presence of a predisposing mutation is indicative that an individual is at increased risk of developing atherosclerosis and/or hyperglycemic disease. The diagnosis of a disease predisposition allows the affected individual to seek early treatment of potential lesions, and to avoid activities that increase risk for cardiovascular disease.

In addition to atherosclerosis and other cardiovascular disease, 5-LO polymorphisms are associated with insulin resistance. Insulin resistance occurs in 25% of non-diabetic, non-obese, apparently healthy individuals, and predisposes them to both diabetes and coronary artery disease. Hyperglycemia in type II diabetes is the result of both resistance to insulin in muscle and other key insulin target tissues, and decreased beta cell insulin secretion. Longitudinal studies of individuals with a strong family history of diabetes indicate that the insulin resistance precedes the secretory abnormalities. Prior to developing diabetes these individuals compensate for their insulin resistance by secreting extra insulin. Diabetes results when the compensatory hyperinsulinemia fails. The secretory deficiency of pancreatic beta cells then plays a major role in the severity of the diabetes.

However, even without developing hyperglycemia and diabetes, these insulin resistant individuals pay a significant price in terms of general health. Insulin resistance results in an increased risk for having elevated plasma triglycerides (TG), lower high density lipoproteins (HDL), and high blood pressure, a cluster of abnormalities that have been termed by different investigators as either Syndrome X, the insulin resistance syndrome, or the metabolic syndrome. It is believed that either the hyperinsulinemia, insulin resistance, or both play a direct role in causing these abnormalities. Data from ethnic, family, and longitudinal studies suggest that a major component of resistance is inherited.

The most practical way of assessing insulin resistance is the homeostasis model assessment (HOMAIR), involving fasting insulin and glucose levels. This value is calculated as fasting plasma insulin (.mu./ml).times.fasting plasma glucose (mmol/L)/22.5 (Matthews et al. (1985) Diabetologia. 28:412–9). The steady-state basal plasma glucose and insulin concentrations are determined by their interaction in a feedback loop. A computer-solved model is been used to predict the homeostatic concentrations that arise from varying degrees beta-cell deficiency and insulin resistance. Comparison of a patient's fasting values with the model's predictions allows a quantitative assessment of the contributions of insulin resistance and deficient beta-cell function to the fasting hyperglycaemia. The estimate of insulin resistance obtained by homeostasis model assessment correlates with estimates obtained by use of the euglycaemic clamp, the fasting insulin concentration, and the hyperglycaemic clamp. The lower limit of the top quintile of HOMA(IR) distribution (i.e. 2.77) in nonobese subjects with no metabolic disorders has been chosen as the threshold for insulin resistance in some studies (Bonora et al. (1998) Diabetes 47:1643–9). The results of this study documented that 1) in hypertriglyceridemia and a low HDL cholesterol state, insulin resistance is as common as in NIDDM, whereas it is less frequent in hypercholesterolemia, hyperuricemia, and hypertension; 2) the vast majority of subjects with multiple metabolic disorders are insulin resistant; 3) in isolated hypercholesterolemia, hyperuricemia, or hypertension, insulin resistance is not more frequent than can be expected by chance alone; and 4) in the general population, insulin resistance can be found even in the absence of any major metabolic disorders.

The measurement of insulin concentration can be done in the overnight fasted condition, since in the postprandial state, glucose levels are changing rapidly and the variable levels of glucose confound the simultaneous measure of insulin levels as an index of insulin action. There is a significant correlation between fasting insulin levels and insulin action as measured by the clamp technique. Very high plasma insulin values in the setting of normal glucose levels are very likely to reflect insulin resistance. As individuals develop diabetes, plasma glucose increases and plasma insulin decreases and so the plasma insulin level no longer reflects only insulin resistance because it becomes influenced by the appearance of a β-cell defect and hyperglycemia.

The 5-LO genes have been found to be differentially expressed in an animal model for atherosclerosis. "Differential expression" as used herein refers to both quantitative as well as qualitative differences in the genes' temporal and/or tissue expression patterns. Thus, a differentially expressed gene may have its expression diminished or inactivated in protective versus susceptible cardiovascular conditions. The 5-LO gene therefore finds use in screening for agents that modulate expression or activity, and which find use in treatment of cardiovascular disease. Drug candidates of interest include known 5-LO inhibitors, many of which are known in the art, for example zileuton, ABT-761 (see Drazen et al., supra.); 2,5-Diaryl tetrahydrofurans, 2,5-diaryl tetrahydrothiophenes, 2,4-diaryl tetrahydrofurans, 2,4-diaryl tetrahydrothiophenes, 1,3-diaryl cyclopentanes, 2,4-diaryl pyrrolidines, and 2,5-diaryl pyrrolidines as disclosed in U.S. Pat. No. 6,294,574; compounds described in U.S. Pat. No. 6,194,585, and the like.

Screening assays identify compounds that modulate the expression or activity of 5-LO or other genes in the leukotriene pathway. A 5-LO inhibitor can, for example, act as the basis for amelioration of such cardiovascular diseases as atherosclerosis, ischemia/reperfusion, hypertension, restenosis, and arterial inflammation. Such compounds may include, but are not limited to peptides, antibodies, or small organic or inorganic compounds. Methods for the identification of such compounds are described below.

Cell- and animal-based systems can act as models for cardiovascular disease and are useful in such drug screening. The animal- and cell-based models may be used to identify drugs, pharmaceuticals, therapies and interventions that are effective in treating cardiovascular disease. In addition, such animal models may be used to determine the $LD_{50}$ and the $ED_{50}$ in animal subjects, and such data can be used to determine the in vivo efficacy of potential cardiovascular disease treatments. Animal-based model systems of cardiovascular disease may include, but are not limited to, non-recombinant and engineered transgenic animals. Non-recombinant, non-genetic animal models of atherosclerosis may include, for example, pig, rabbit, or rat models in which the animal has been exposed to either chemical wounding through dietary supplementation of LDL, or mechanical wounding through balloon catheter angioplasty, for example. Additionally, animal models exhibiting cardiovascular disease symptoms may be engineered by utilizing, for example, 5-LO gene sequences in conjunction with techniques for producing transgenic animals that are well known to those of skill in the art. For example, target gene sequences may be introduced into, and knocked out or overexpressed in the genome of the animal of interest. Animals of any species, including, but not limited to, mice, rats, rabbits, guinea pigs, pigs, micro-pigs, goats, and non-human primates, e.g., baboons, monkeys, and chimpanzees may be used to generate cardiovascular disease animal models.

Any technique known in the art may be used to introduce a target gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc.

Specific cell types within the animals may be analyzed and assayed for cellular phenotypes characteristic of cardiovascular disease. In the case of monocytes, such phenotypes may include but are not limited to increases in rates of LDL uptake, adhesion to endothelial cells, transmigration, foam cell formation, fatty streak formation, and production of foam cell specific products. Further, such cellular phenotypes may include a particular cell type's fingerprint pattern of expression as compared to known fingerprint expression profiles of the particular cell type in animals exhibiting cardiovascular disease symptoms.

Cells that contain and express 5-LO can be utilized to identify compounds that exhibit anti-cardiovascular and/or anti-hyperglycemic disease activity. In the case of monocytes, such phenotypes may include but are not limited to increases in rates of LDL uptake, adhesion to endothelial cells, transmigration, foam cell formation, fatty streak formation, and production by foam cells of growth factors such as bFGF, IGF-I, VEGF, IL-1, M-CSF, TGFβ, TGFα, TNFα, HB-EGF, PDGF, IFN-γ and GM-CSF. Transmigration rates, for example, may be measured using an in vitro system to quantify the number of monocytes that migrate across the endothelial monolayer and into the collagen layer of the subendothelial space.

Cells of a cell type known to be involved in cardiovascular and/or hyperglycemic disease may be transfected with sequences capable of increasing or decreasing the amount of 5-LO gene expression within the cell. For example, 5-LO gene sequences may be introduced into, and overexpressed in, the genome of the cell of interest, or, if endogenous target gene sequences are present, they may be either overexpressed or, alternatively disrupted in order to underexpress or inactivate target gene expression.

Transfection of target gene sequence nucleic acid may be accomplished by utilizing standard techniques. Transfected cells can be evaluated for the presence of the recombinant 5-LO gene sequences, for expression and accumulation of 5-LO gene mRNA, and for the presence of recombinant 5-LO protein. Where a decrease in 5-LO gene expression is desired, standard techniques may be used to demonstrate whether a decrease in expression is achieved.

In vitro systems may be designed to identify compounds capable of inhibiting 5-LO. Such compounds may include, but are not limited to, peptides made of D-and/or L-configuration amino acids, phosphopeptides, antibodies, and small organic or inorganic molecules. The principle of the assays used to identify compounds that inhibit 5-LO involves preparing a reaction mixture of 5-LO and a test compound under conditions and for a time sufficient to allow the two components to interact, and detecting the resulting change in the catalytic activity in the formation of leukotrienes. Alternatively, a simple binding assay can be used as an initial screening method. These assays can be conducted in a variety of ways. For example, one method to conduct such an assay would involve anchoring 5-LO protein or a test substance onto a solid phase and detecting complexes anchored on the solid phase at the end of the reaction. In another embodiment of such a method, the assay tests the presence of products catalyzed by 5-LO.

For example, a routine assay of 5-LO activity can be performed in a mixture containing 50 mM potassium phosphate buffer at pH 7.4, 2 mM $CaCl_2$, 2 mM ATP, 25 M arachidonic acid (0.1 Ci) and 5-LO enzyme (50–100 mg of protein) in a final volume of 200 ml. The reaction is carried out at 24° C. for 3 minutes. The mixture is extracted with 0.2 ml of an ice-cold mixture of ethyl ether:methanol: 0.2 M citric acid (30:4:1). The extract is subjected to thin-layer chromatography at −10° C. in a solvent system of petroleum ether:ethyl ether:acetic acid (15:85:0.1). The silica gel zones corresponding to authentic arachidonic acid and its metabolites are scraped into scintillation vials for counting. The enzyme activity is expressed in terms of the amount of arachidonic acid oxygenated for 3 minutes.

In a binding assay, the reaction can be performed on a solid phase or in liquid phase. In a solid phase assay, the nonimmobilized component is added to the coated surface containing the anchored component. After the reaction is complete, unreacted components are removed under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a binding reaction can be conducted in a liquid phase, the reaction products separated from unreacted components, and complexes detected; e.g., using an immobilized antibody specific for target gene product or the test compound to anchor any complexes formed in solution, and a labeled antibody specific for the other component of the possible complex to detect anchored complexes.

Cell-based systems such as those described above may be used to identify compounds that act to ameliorate cardiovascular disease symptoms. For example, such cell systems may be exposed to a test compound at a sufficient concentration and for a time sufficient to elicit such an amelioration of cardiovascular disease symptoms in the exposed cells. After exposure, the cells are examined to determine whether one or more of the cardiovascular disease cellular phenotypes has been altered to resemble a more normal or more wild type, non-cardiovascular disease phenotype. For example, and not by way of limitation, in the case of monocytes, such more normal phenotypes may include but are not limited to decreased rates of LDL uptake, adhesion to endothelial cells, transmigration, foam cell formation, fatty streak formation, and production by foam cells of growth factors such as bFGF, IGF-I, VEGF, IL-1, M-CSF, TGFβ, TGFα, TNFα, HB-EGF, PDGF, IFN-γ and GM-CSF.

In addition, animal-based disease systems, such as those described, above may be used to identify compounds capable of ameliorating disease symptoms. Such animal models may be used as test substrates for the identification of drugs, pharmaceuticals, therapies, and interventions, which may be effective in treating disease. For example, animal models may be exposed to a compound, suspected of exhibiting an ability to ameliorate cardiovascular disease symptoms, at a sufficient concentration and for a time sufficient to elicit such an amelioration of disease symptoms in the exposed animals. The response of the animals to the exposure may be monitored by assessing the reversal of disorders associated with disease, for example, by counting the number of atherosclerotic plaques and/or measuring their size before and after treatment.

With regard to intervention, any treatments that reverse any aspect of cardiovascular disease symptoms or insulin resistance and other hyperglycemic conditions should be considered as candidates for human disease therapeutic intervention. Dosages of test agents may be determined by deriving dose-response curves.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The methods described herein may be performed, for example, by utilizing pre-packaged diagnostic kits comprising at least one specific 5-LO nucleic acid reagent described herein, which may be conveniently used, e.g., in clinical settings, for prognosis of patients susceptible to cardiovascular disease.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

EXPERIMENTAL

Atherosclerosis is initiated by the trapping and oxidation of low-density lipoproteins (LDL) in the subendothelial layer of the artery wall, resulting in the formation of biologically active species that stimulate vascular cells to produce inflammatory molecules. This signals a cascade of leukocyte recruitment, further lipoprotein oxidation, foam cell formation, necrosis, and fibroproliferation. To identify genes that contribute to this complex process, we previously constructed a cross between an atherosclerosis-resistant mouse strain, CAST, and a susceptible strain, B6. A major locus for atherosclerosis was identified on mouse chromosome 6 and was subsequently confirmed with the congenic strain designated CON6 in which the central region of chromosome 6 from CAST was bred onto a B6 background. These CON6 mice had reduced insulin levels and dramatically decreased lesion formation when bred onto an LDL receptor-null (LDLR-/-) background and fed an atherogenic diet. Moreover, bone marrow transplantation studies indicated that the resistant phenotype was conferred in part by bone marrow-derived cells.

In examining the congenic region for potential positional candidate genes, we observed that 5-lipoxygenase (5-LO) mapped directly underneath the linkage peak for the locus. 5-LO is the rate-limiting enzyme in leukotriene (LT) biosynthesis and is expressed primarily in leukocytes, including monocytes and macrophages. Leukotrienes are potent proinflammatory lipid mediators derived from arachidonic acid and have been shown to affect several pathophysiological conditions. Therefore, 5-LO could potentially contribute to the development of atherosclerosis through lipid oxidation and/or inflammatory processes. The contribution of 5-LO to atherosclerotic lesion formation was examined, based on its location within the chromosome 6 congenic region, its role in inflammation, and its expression in leukocytes. The results indicate that 5-LO participates in atherogenesis.

Materials and Methods

Animal Husbandry. Mice were purchased from the Jackson Laboratories, Bar Harbor, Me., and housed 4 per cage at 25° C. on a 12-hour light/dark cycle. They were maintained either on a chow diet or a high-fat, high-cholesterol diet containing 15% fat, 1.25% cholesterol, and 0.5% cholic acid (diet No. 90221, Harlan-Teklad). The mice used in the experiments described below were of both sexes and between 4 to 6 months of age. All procedures were in accordance with current National Institutes of Health guidelines and were approved by the UCLA Animal Research Committee.

5-LO$^{-/-}$ mice on a B6 background were generated as described previously. To generate double knockout animals, 5-LO$^{-/-}$ mice were first bred to LDLR$^{-/-}$ mice (also on a B6 background), and the F1 progeny were backcrossed to LDLR$^{-/-}$ mice to produce 5-LO$^{+/-}$/LDLR$^{-/-}$ mice. These mice were then intercrossed to generate double knockout animals. Although a small number of 5-LO$^{-/-}$/LDLR$^{-/-}$ mice were obtained, they did not produce offspring. Therefore, the experiments described herein were performed with 5-LO$^{+/-}$/LDLR$^{-/-}$ mice. The segregation of the 5-LO$^{-/-}$ mutation was followed using PCR primers specific for the targeted allele (neo primer) SEQ ID NO:1 5'-ATCGCCT-TCTTGACGAGTTC-3'; downstream primer for both +/+ and KO within intron 6 SEQ ID NO:2 5'-GCAGGAAGTG-GCTACTGTGGA-3'; primer specific to +/+ 5' SEQ ID NO:3 TGCAACCCAGTACTCATCAAG-3'. PCR primers used for the LDLR+/+ allele were SEQ ID NO:4 5'-AC-CCCAAGACGTGCTCCCAGGATGA-3' and SEQ ID NO:5 5'-CGCAGTGCTCCTCATCTGACTTGT-3' and for the mutant allele were SEQ ID NO:6 5'-AG-GATCTCGTCGTGACCCATGGCGA-3' and SEQ ID NO:7 5'-GAGCGGCGATACCGTAAAGCACGAGG-3'.

Plasma Lipid and Insulin Measurements. Mice were fasted overnight and bled retro-orbitally under isoflurane anesthesia. Enzymatic assays for plasma cholesterol levels were performed as described previously. Insulin levels were measured in duplicate by ELISA (Crystal Chemical IUSKRO20).

Northern Blot Analysis Total RNA was isolated from bone marrow cells using Trizol reagent (Life Technologies Inc). The RNA (10 μg) was run on a 1% agarose formaldehyde gel, transferred to nylon membrane, and hybridized with a 700-bp mouse-specific probe from the 3' end of the 5-LO cDNA. The blots were stripped and probed for GAPDH as an internal control. Levels of 5-LO mRNA were quantitated by phosphorimaging and are expressed as the ratio of 5-LO to GAPDH mRNA.

Western Blot Analysis. Homogenates of bone marrow cells (80 μg protein) in SDS sample buffer were subjected to electrophoresis on NuPAGE 4% to 12% precast SDS polyacrylamide gradient gels (Novex) under reducing conditions as suggested by the manufacturer. Proteins were transferred to nitrocellulose membranes, incubated (1:3000 dilution) overnight with antibodies to 5-LO, LTA4 hydrolase, or LTB4 omega-hydroxylase (Cayman Chemical), and visualized by ECL detection (Amersham, Little Chalfont). Image-Quant software (Molecular Dynamics) was used for the quantification of bands, which were normalized to GAPDH.

Measurement of LTB4 Levels. LTB4 levels were determined in duplicate using a commercially available ELIZA kit (Cayman Chemical). Assays were performed on bone marrow cells (25 μg protein) homogenized in 10 mmol/L Tris, pH 8.0.

Sequence Analysis of 5-LO cDNA. cDNA was prepared from peritoneal macrophage RNA of CAST and B6 mice using an Superscript rtPCR kit (Gibco BRL). The PCR primers used for sequencing were as follows: SEQ ID NO:8 5-'ATGCCCTATGCCCTCCTACACTGTCAC-3'/SEQ ID NO:9 5'-CCACTCCATCCATCTATACTG-3'; SEQ ID NO:10 5'-GCAGCACAGACGTAAAGAACTG-3'; SEQ ID NO:11 5'-GAGGAAGTCACTGGAACGCAC; SEQ ID NO:12 5'-CTACGGATTCAAAGTACGACTG-3'/SEQ ID NO:13CAGGTACTCGGACAGCTTCTC-3'; SEQ ID NO:14 5'-GCTATCCAGTCGTTCACGATG-3' SEQ ID NO:15 5'-GCAGCACTTCGAGCTTGGAAG-3'. The products were purified and sequenced by Laragen, Inc. (Los Angeles). The results were analyzed by the use of programs available through NCBI.

Isolation of Bone Marrow Cells and Peritoneal Macrophages. Bone marrow cells were flushed from mouse femurs with DMEM/5% fetal calf serum (FCS) and centrifuged at 1500 RPM for 15 minutes (3 repetitions of washing and centrifugation). Peritoneal macrophages were isolated after lavage with DMEM/5% FCS, as described for bone marrow cells.

Measurement of 5-LO by Immunohistochemistry. Immunostaining was performed on aortic lesion cryostat sections from apolipoprotein E$^{-/-}$ (apoE$^{-/-}$) and LDLR$^{-/-}$ mice, as described below. Alternate sections were fixed with formaldehyde, washed with PBS, and incubated in blocking buffer, followed by either rabbit anti-human 5-LO (Cayman Chemical, Mich) or rat anti-mouse MOMA-2 (Accurate Chemical, NY) antiserum. The sections were then washed and incubated with biotinylated goat anti-rabbit IgG at a dilution of 1:200. After extensive washing, the macrophages and 5-LO protein were visualized by alkaline phosphatase using Vector Red as substrate. Appropriate control experiments, including omission of primary antibody, were performed. Peritoneal monocyte/macrophages were harvested with 20 mL DMEM/5% FCS 3 days after 4% thioglycolate (DIFCO, MI) injection. The cells were centrifuged at 1500 rpm, washed 3 times with media, and cultured overnight on glass slides. The slides were stained with a 1:200 dilution of rabbit anti-human 5-LO and hematoxylin.

Aortic Lesion Analysis After 8 weeks on a high-fat, high-cholesterol diet, mice were euthanized and the upper portion of the heart and proximal aorta were removed, embedded in OCT compound (Miles Laboratories), and stored at −70° C. Serial 10 μm-thick cryosections from the middle portion of the left ventricle of the aortic arch were collected and mounted on poly-D-lysine-coated plates. Sections were stained with oil red O and hematoxylin, and the lipid staining areas were counted in a blinded fashion by light microscopy.

Bone Marrow Transplantation. Four-month-old LDLR$^{-/-}$ mice were used as recipients for bone marrow transplanted from either 3-month-old 5-LO$^{+/-}$/LDLR$^{-/-}$ mice or control LDLR$^{-/-}$ mice. Recipient mice were lethally irradiated and then injected with $10^7$ bone marrow cells through the tail vein, as described previously. Four weeks after transplantation, DNA from blood-derived leukocytes was analyzed for the presence of the targeted 5-LO allele, and the animals were placed on the high-fat, high-cholesterol diet for 8 weeks.

Statistical Analyses. Differences in measured variables between groups of mice were determined by ANOVA (Statview version 5.0). Values are expressed as mean±SEM, and differences were considered statistically significant at P±0.05.

Results

CON6 Mice Have Reduced Expression of 5-LO. Quantitative trait locus mapping of a cross between resistant CAST and susceptible B6 mice for atherosclerotic lesion development revealed a locus with a powerful effect on atherosclerosis on mouse chromosome 6. Subsequently, a congenic strain, CON6, containing the locus derived from CAST on the background of B6 was constructed. The congenic strain was almost entirely resistant to atherosclerosis, even when an LDL receptor-null mutation was introduced. These studies defined the critical region of the gene to between ~45 cM and 74 cM on mouse chromosome 6. To complement this approach, various candidate genes within the locus were tested. The 5-LO gene is located near the middle of the congenic region, at ~53 cM.

Given the proinflammatory properties of 5-LO and leukotrienes, it was reasoned that variation in the 5-LO gene could be involved in the resistance to atherosclerosis of the CON6 mice. To examine this possibility, the expression of mRNA for 5-LO was quantitated in bone marrow cells, a tissue previously shown to synthesize 5-LO. Northern blot analysis was performed using a mouse 5-LO cDNA probe and the signal was quantitated using a PhosphorImager and GAPDH as an internal control.

Figure 1B:
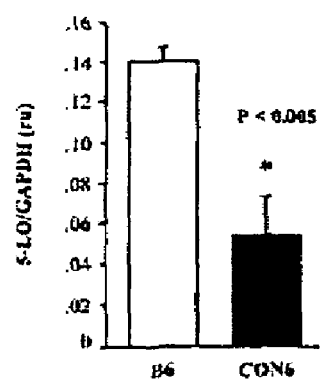
Figure 2A:
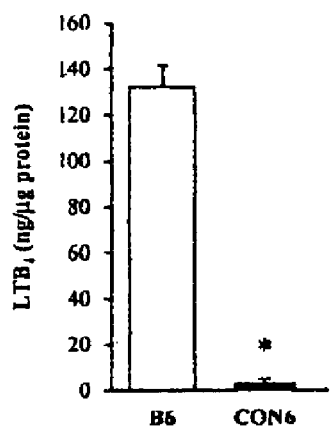
FIGS. 2A and 2B. Levels of LTB4, LTA4 hydrolase, and LTB4 ω-hydroxylase in CON6 and B6 mice. A, LTB4 levels in bone marrow cells of B6 (n=3) and CON6 (n=3) mice were determined by ELIZA (Cayman Chemical). B, Levels of LTA4 hydrolase and LTB4 hydroxylase of B6 (n=3) and CON6 (n=3) were determined after immunoblot analysis using specific, commercially available antibodies (Cayman Chemical). Data are from 4- to 6-month-old animals on a chow diet and are representative of at least 3 experiments.
Figure 2B:
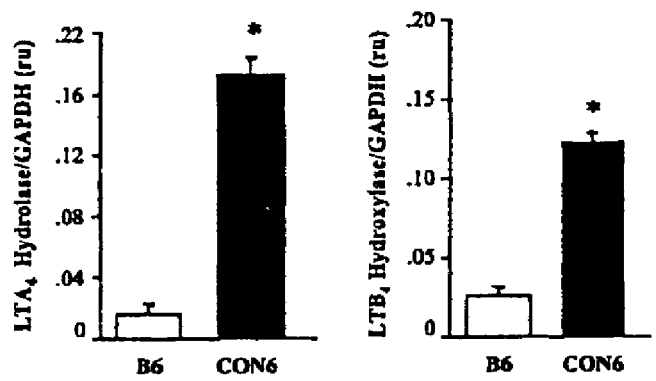

As shown in FIG. 1A, CON6 mice on an LDL receptor-null background exhibited only about 15% of the mRNA levels of LDLR$^{-/-}$ mice. Similarly, CON6 mice exhibited a very significant reduction in 5-LO protein levels compared with B6 controls, as determined by immunoblot analysis (FIG. 1B). Densitometric analysis of the blots indicated that CON6 mice have approximately 25% of the levels of 5-LO protein as B6 mice. 5-LO catalyzes the oxidation of arachidonic acid to 5-HPETE and LTA4, which is then converted to LTB4 by LTA4 hydrolase. As measured by ELIZA assay, LTB4 levels in CON6 mice were only a few percent of those in B6 mice (FIG. 2A), demonstrating that 5-LO activity is also reduced in CON6 mice. LTA4 hydrolase and LTB4 ω-hydroxylase are 2 downstream enzymes from 5-LO and were also examined in bone marrow cells by immunoblot analysis (FIG. 2B). The protein levels of LTA4 hydrolase and LTB4 ω-hydroxylase were both increased in CON6 versus B6 mice, suggesting that these enzymes are upregulated in response to decreased 5-LO levels.

Sequence Variation Between B6 and CAST 5-LO cDNA. The 5'UTR and coding region of 5-LO cDNA were sequences from B6 and CAST mice to examine possible variations that could influence the enzyme's synthesis and/or function. The 5-LO sequence is highly conserved between the 2 strains with only 6 nucleotide changes, 4 of which did not result in amino acid substitution. The 2 amino acid changes occurred at residue 645, where B6 has an isoleucine and CAST has a valine, and at 646, where B6 has a valine and CAST has an isoleucine.

5-LO Is Expressed in Atherosclerotic Lesions and in Macrophages. To determine whether 5-LO is present in atherosclerotic lesions, immunohistochemical studies of mouse aortic sections were per-formed. The proximal aortas (from the aortic root up to the aortic arch) of apoE$^{-/-}$ and LDLR$^{-/-}$ mice were sectioned and stained with antibody to either 5-LO or the macrophage-specific marker, MOMA-2 (FIG. 3). As expected, staining with oil red O revealed the presence of large lipid-filled areas and a necrotic core within the lesions of both apoE$^{-/-}$ and LDLR$^{-/-}$ mice. Staining with MOMA-2, a macrophage-specific marker also revealed sites of infiltration of monocyte/macrophages into the subendothelial space (3A-C). The adjacent sections, stained with 5-LO antibody, revealed abundant 5-LO protein staining that appeared to colocalize, at least in part, with a subset of monocyte/macrophages (FIGS. 3D through 3F). Interestingly, 5-LO staining was not present in all regions containing monocyte/macrophages, as evident from the LDLR$^{-/-}$ sections (3C and F). We next tested whether the expression of 5-LO in macrophages from CON6 and B6 mice by immunostaining the cells with antiserum against 5-LO. As shown in FIG. 4, B6 macrophages exhibited significant 5-LO staining, whereas CON6 macrophages had dramatically reduced staining.

Deficiency of 5-LO Dramatically Reduces Atherosclerosis in an LDLR$^{-/-}$ Model. Given the dramatically reduced size of aortic lesions and reduced expression of 5-LO in CON6 mice, shown in Table 1, we assessed the involvement of 5-LO in lesion development by examining atherosclerosis in 5-LO knockout mice, previously constructed by Funk and colleagues.

Figure 5:
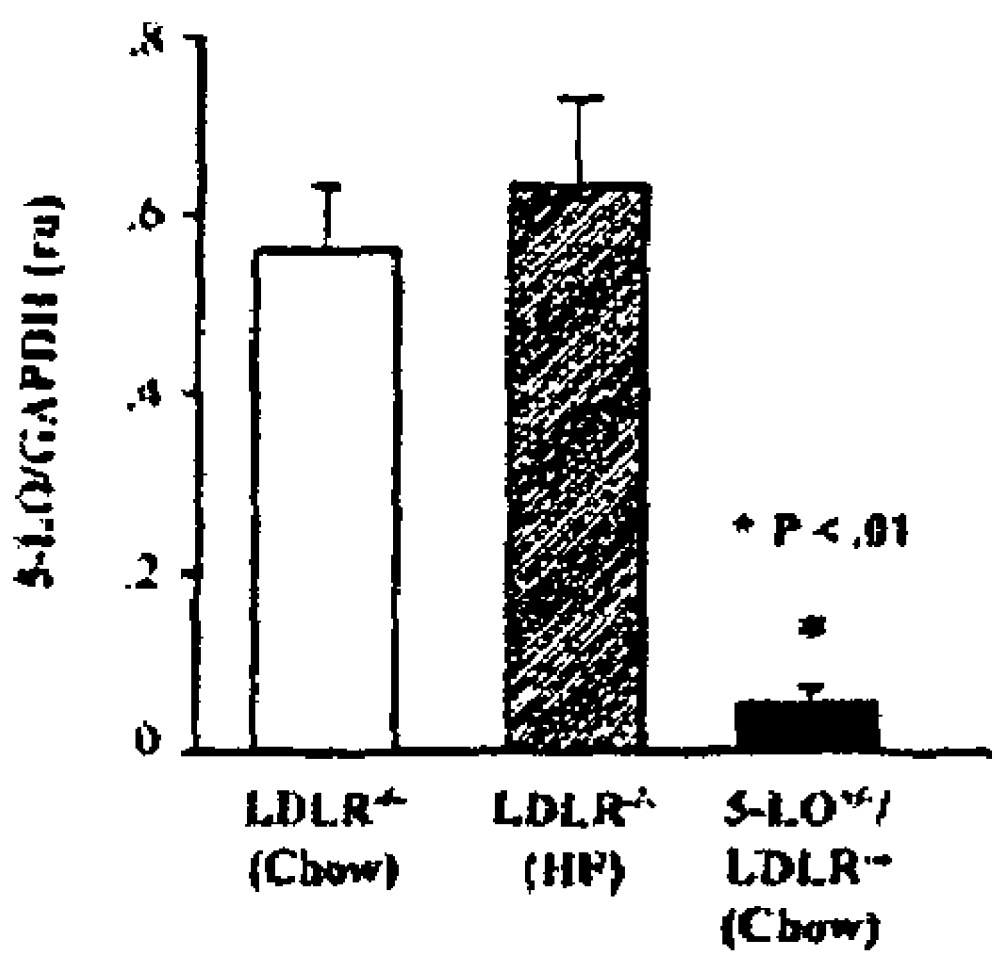
FIG. 5. Decreased 5-LO protein in 5-LO+/−/LDLR−/− mice compared with LDLR−/− controls. Immunoblot analysis of bone marrow cells stained with rabbit anti-human 5-LO antibody indicates that 5-LO+/−/LDLR−/− mice (n=3) have an approximately 90% reduction in 5-LO protein compared with control LDLR−/− mice (n=3). Data are from 4- to 6-month-old animals on a chow or high-fat diet. Levels of 5-LO protein did not differ in LDLR−/− mice on either a chow or high-fat (HF) diet.

5-LO-null mice were bred on a B6 background, with LDL receptor-null mice, also on a B6 background. The frequency of double knockout mice was much lower than expected based on Mendelian segregation, presumably because the two mutations are incompatible with life. Because the CON6 mice exhibited reduced, but not absent, 5-LO activity, we examined mice heterozygous for the 5-LO-null mutation on an LDL receptor-null background. 5-LO protein levels did not differ in LDL$^{-/-}$ mice fed either a chow or high-fat, high-cholesterol diet (FIG. 5). However, there were decreased levels of 5-LO mRNA (FIG. 1A) and protein (FIG. 5) in the 5-LO$^{+/-}$/LDL$^{-/-}$ mice compared with LDLR$^{-/-}$ mice on a chow diet, which was less than the 50% that would be expected from heterozygotes. Because homozygous double knockout mice were not obtained either, it is possible that there is an interaction between LDLR and 5-LO such that disruption of both leads to altered expression of one or both genes as well as incompatibility with life.

Figure 6A:
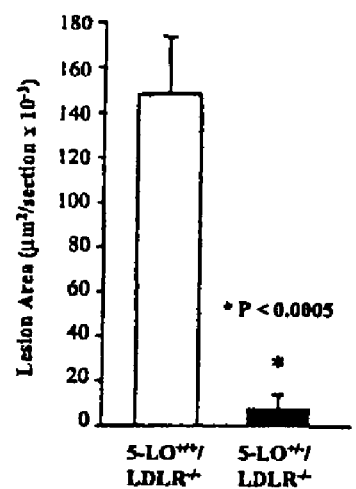
FIGS. 6A and 6B. 5-LO-null mutation decreases aortic lesions even in the presence of elevated total cholesterol levels. Four- to six-month-old 5-LO+/− (n=4) and 5-LO+/+ (n=4) mice on an LDLR−/− background fed a high-fat, high-cholesterol diet for 8 weeks have over a 26-fold decrease in lesion formation, despite cholesterol levels that exceeded 500 mg/dL. There were no significant differences in the levels of LDL/VLDL-cholesterol.
Figure 6B:
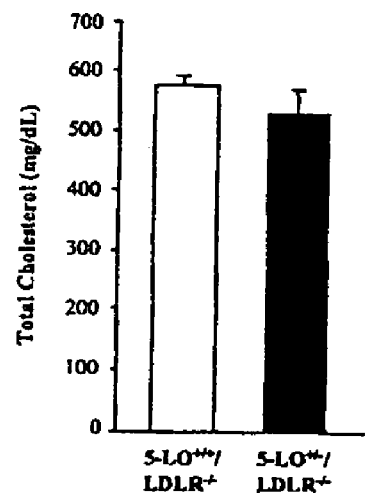

After feeding of an atherogenic diet for 8 weeks, a striking effect of 5-LO on atherosclerosis was observed. As expected, the 5-LO$^{+/+}$/LDLR$^{-/-}$ control mice had large advanced lesions, with an average area of 153,080±21,010 μm$^2$. The 5-LO$^{+/-}$/LDLR$^{-/-}$ mice, on the other hand, had an aortic lesion area of only 5830±2080 μm$^2$ (FIG. 6A). Thus, mice heterozygous for the 5-LO-null mutation had over a 26-fold decrease (P<0.0005) in lesion size despite having cholesterol levels similar to LDLR$^{-/-}$ mice, exceeding 500 mg/dL (FIG. 6B). This reduction in atherosclerosis was very similar to what we previously observed when the CON6 locus was transferred onto the LDLR$^{-/-}$ background 3 and indicates that 5-LO has a dose-dependent effect on lesion size.

Figure 7:
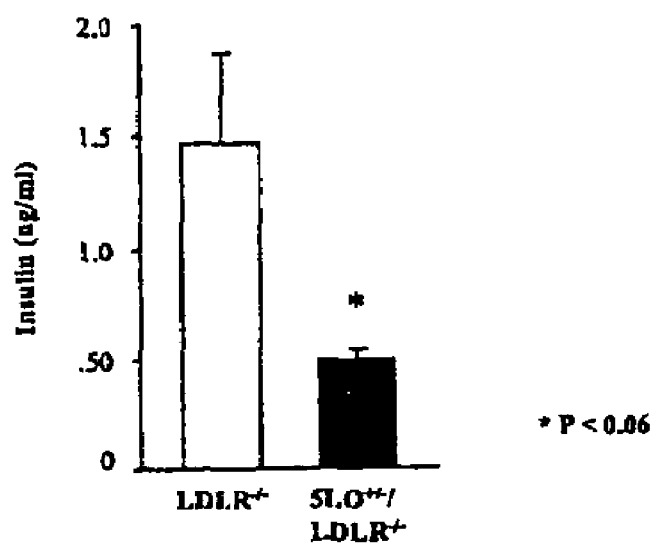
FIG. 7. Plasma insulin levels in 5-LO+/−/LDLR−/− mice compared with LDLR−/− controls. Insulin levels from 4- to 6-month-old 5-LO+/−/LDLR−/− (n=5) and 5LO+/+/LDLR−/− (n=5) mice on a chow diet were determined by immunoassay as described in Materials and Methods. Mice fed a high-fat, high-cholesterol diet (n=5 for each genotype) had similar differences.

5-LO$^{+/-}$ Mice on an LDLR$^{-/-}$ Background Have Reduced Insulin Levels. In previous studies of the CAST B6 intercross, we observed a significant quantitative trait locus for insulin levels on chromosome 6 that was coincident with the locus for lesion formation. Moreover, the CON6 strain exhibited decreased insulin levels as compared with B6 mice. To examine whether 5-LO could also account, in part, for the linkage of insulin to this locus, we measured insulin levels in the 5-LO$^{+/-}$/LDLR$^{-/-}$ mice. Analogous to the lesion results, heterozygosity for a 5-LO-null allele on an LDL$^{-/-}$ background decreased insulin levels 3-fold compared with 5-LO$^{+/+}$/LDLR$^{-/-}$ controls (FIG. 7). This suggests that variations of the 5-LO gene may also have a role in regulation of insulin levels associated with this locus.

Bone Marrow Transplantation of the 5-LO$^{+/-}$ Allele Confers Resistance to Atherosclerosis. We previously demonstrated that transplantation of CON6 bone marrow into B6 mice resulted in an approximate 2-fold decrease in lesion formation, consistent with the concept that the genetic variation between CON6 and B6 strains is due, in part, to leukocyte functions. To test whether 5-LO$^{+/-}$ mice exhibited a similar bone marrow-dependent effect on atherosclerosis, we transplanted either 5-LO$^{+/-}$/LDLR$^{-/-}$ or 5-LO$^{+/+}$/LDLR$^{-/-}$ LDL receptor-deficient mice. Successful transplantation was confirmed 4 weeks after the procedure, as previously described. After 8 weeks on a high-fat, high-cholesterol diet, 5-LO mRNA remained significantly decreased in peritoneal macrophages from LDLR$^{-/-}$ mice transplanted with 5-LO$^{+/-}$/LDLR$^{-/-}$ marrow, indicative of successful bone marrow transplantation.

Figure 8A:
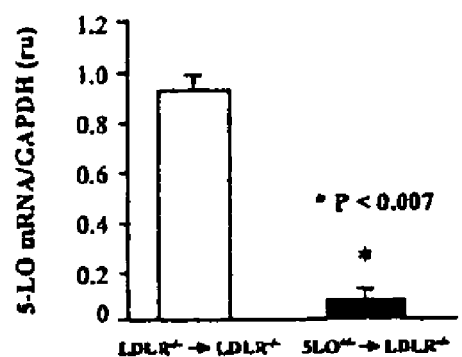
FIGS. 8A and 8B. LDLR−/− mice transplanted with 5-LO+/− bone marrow exhibit decreased 5-LO mRNA levels in bone marrow cells and have reduced atherosclerotic lesions. Four-month-old LDLR−/− mice transplanted with either 5-LO+/−/LDLR−/− or LDLR−/− bone marrow were allowed to recover for 4 weeks and then fed an atherogenic diet for 8 weeks. Nine mice of each genotype were examined for (A) levels of 5-LO mRNA from bone marrow cells by Northern blot analysis and (B) aortic lesions as described for FIG. 6.
Figure 8B:
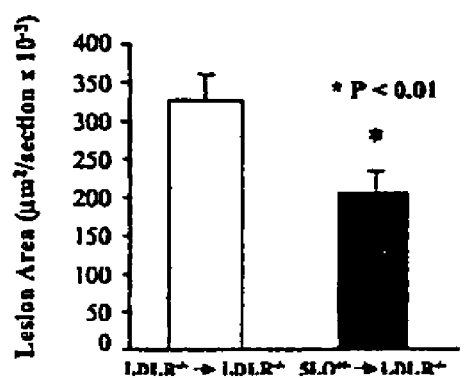

Consistent with the CON6 findings, LDLR$^{-/-}$ mice receiving 5-LO$^{+/-}$ bone marrow exhibited a 2-fold decrease in atherosclerosis compared with controls (FIGS. 8A and 8B), suggesting that the 5-LO in macrophages is involved in lesion formation. Presumably, artery wall cells other than those derived from bone marrow are also involved in atherosclerosis, which may explain why transplantation of 5-LO-deficient bone marrow does not decrease lesions to the same extent as global disruption of 5-LO$^{+/-}$.

The present study provides compelling evidence that the positional candidate gene, 5-LO, is involved in the development of atherosclerotic lesions. Most significantly, heterozygous deficiency for the enzyme in a knockout model decreased lesion size in LDLR$^{-/-}$ mice by about 95%, an effect far greater than any other gene, with the possible exception of macrophage colony stimulating factor (MCSF). The enzyme was expressed abundantly in macrophage-rich regions of atherosclerotic lesions, suggesting that 5-LO and/or its products may act locally to promote lesion development. There are a number of potential mechanisms by which these products may act. These include the following: seeding of LDL by oxidation products produced by the 5-LO pathway; the production of natural ligands for nuclear receptors, such as peroxisome proliferator-activated receptor α (PPARα); and various autocrine and paracrine effects mediated through G protein-associated primary receptors for leukotrienes. Such effects could potentially influence specific immunity functions, such as the differentiation and migration of other cells.

It is interesting to note that transplantation of 5-LO-deficient bone marrow did not decrease atherosclerosis to the same extent as that observed in the 5-LO$^{+/-}$ mice. One explanation is that the host myeloid cells may not all be totally abolished, even with irradiation of the recipient before transplantation. Subsequent blood cells in the recipient would thus not be derived entirely from the donor. In addition, certain lymphocytes and the Kupffer cells of the liver, which have long half-lives, would not be replaced as a result of transplantation and still remain from the recipient. Lastly, 5-LO is expressed in endothelial cells, albeit at very low levels, which could continue to promote lesion development and the inflammatory state of the artery wall even in the absence of macrophage 5-LO. In contrast, global disruption of 5-LO would presumably decrease its expression in endothelial cells to an even greater extent than that in macrophages and thus account for the greater reduction of atherosclerosis observed in the 5-LO knockout mice.

Our studies also provide strong presumptive evidence that variations of the 5-LO gene explain the resistance to atherosclerosis observed in CON6 mice. This possibility is supported by the following lines of evidence: (1) 5-LO is a reasonable candidate based on its known proinflammatory properties; (2) 5-LO is expressed in macrophage-rich regions of mouse lesions; (3) 5-LO is decreased similarly in CON6 mice and heterozygous 5-LO knockout mice, and both have a similar, dramatic effect on atherosclerosis; (4) insulin levels are decreased in both CON6 and heterozygous 5-LO knockout mice; and (5) bone marrow transplantation of CON6 or heterozygous 5-LO knockout bone marrow had a similar (-2- to 3-fold decrease) effect on atherosclerosis in LDLR$^{-/-}$ mice.

Although the most straightforward explanation for the effect of 5-LO on atherosclerosis in CON6 mice is the decreased expression, it is possible that structural differences also contribute. Sequencing of B6 and CAST 5-LO cDNA revealed two amino acid differences between the two strains at positions 645 (CAST/Val; B6/Ile) and 646 (CAST/Ile; B6/Val). 5-LO is highly conserved among mammals and the human and rat sequences are identical with that of B6 at positions 645 and 646. It is not known whether these substitutions influence 5-LO function but they may influence the cellular trafficking of 5-LO. For example, these two residues are within a conserved region of basic amino acids, from positions 639 to 656, found in many proteins that translocate from the cytosol to the nucleus. A synthetic 639 to 656 fusion peptide showed that this potential nuclear localization sequence (NLS) in 5-LO acts as a regulatory domain involved in the nuclear translocation of the enzyme from the cytosol. In contrast, using a synthetic fusion peptide containing the last 90 amino acids of the 5-LO C-terminus, this peptide was not able to translocate into the nucleus. Due to the high conservation of this sequence in proteins containing a NLS, these amino acid substitutions could be potentially important in regulating the translocation of 5-LO to the nucleus.

The process by which atherosclerosis develops in the artery wall is complex and involves a variety of steps, such as lipid oxidation and leukocyte migration/proliferation. Studies in mice suggest that 12/15-LO is an important mediator of atherosclerosis, presumably due to "seeding" LDL with reactive oxygen species, leading to the production of proinflammatory LDL. The eicosanoid products of 5-LO could similarly promote lipoprotein oxidation, thereby contributing to inflammation and foam cell formation. 5-LO and its products have also been implicated in the chemotaxis of leukocytes, which may provide another mechanism for its proinflammatory role in atherosclerosis. For example, 5-HETE exhibits chemotactic activity, al-though only at relatively high concentrations. In neutrophils, dendritic cells, and monocyte/macrophages, 5-HETE can be converted to 5-oxo-ETE,19,20 which is ~10-fold more potent than 5-HETE in stimulating monocyte migration. Moreover, both 5-oxo-ETE and 5-HETE have been shown to synergistically induce monocyte migration in response to monocyte chemotactic protein-1 (MCP-1). These results become more relevant because LTB4 and MCP-1 levels have been show to cross-regulate each other. Studies have shown that intraperitoneal injection of MCP-1 induces production of LTB4, whereas MCP-1 stimulates the production of LTB4 from mouse peritoneal macrophage in a dose-dependent manner. These studies suggest that 5-LO and its product LTB4 could promote atherosclerosis by recruiting monocytes to the vessel wall.

Several mechanisms have been proposed for LTB4 activation of inflammatory responses, including the binding and activation of PPARα and direct G protein signaling pathways mediated by the leukotriene receptors. PPARα is expressed in all vascu-lar cells and could play a role in vascular inflammation. For example, PPARα mediates MCP-1 synthesis in mouse aortic endothelial cells when stimulated with minimally modified LDL or oxidized phospholipids. LTB4 is one of the ligands that activates PPARα and binds with an affinity in the nanomolar range. In addition, each leukotriene has a specific high-affinity G protein-coupled cell surface receptor, which can influence differentiation, migration, and immune functions. For example, LTB4 receptor-null mutants had significant defects in neutrophil and macrophage recruitment and exhibited altered cellular function, such as changes in calcium flux. Thus, 5-LO and its metabolites may play an important role in atherosclerosis either as natural nuclear receptor ligands or through receptor-mediated inflammatory signaling pathways.

Example 2

Based on the above mouse studies, the contribution of the 5LO gene to human atherosclerosis was assessed. These results demonstrate that 5LO is also involved in susceptibility to coronary artery disease (CAD) and diabetes in humans. For example, we observed that certain forms of the 5LO gene (termed deleted alleles) are found in CAD patients three times as often as they are in control subjects (9% vs. 3%; P<0.04; Table 2). The nomenclature for the 5-LO genotype is as discussed in Drazen et al. (1999), supra. The genotype is determined by the number of Sp1 repeats in the promoter region, where 3 and 4 repeats are referred to as a "D", or deleted allele. 5 repeats is the "N", or normal allele; and 6 repeats is an "A", or addition allele. The genotyping is performed essentially as set forth in Drazen et al. Even though the at-risk group is only ~9% of the population, this has very significant health care implications since CAD is so prevalent.

TABLE 2

CAD and 5-LO Genotype

| | No CAD | Yes CAD | Total |
|---|---|---|---|
| DD | 16 | 5* | 21 |
| DN | 132 | 18 | 150 |
| NN | 350 | 32 | 382 |
| Total | 498 | 55 | 553 |

*P value is 0.04, $X^2$ = 6.263

Figure 9:
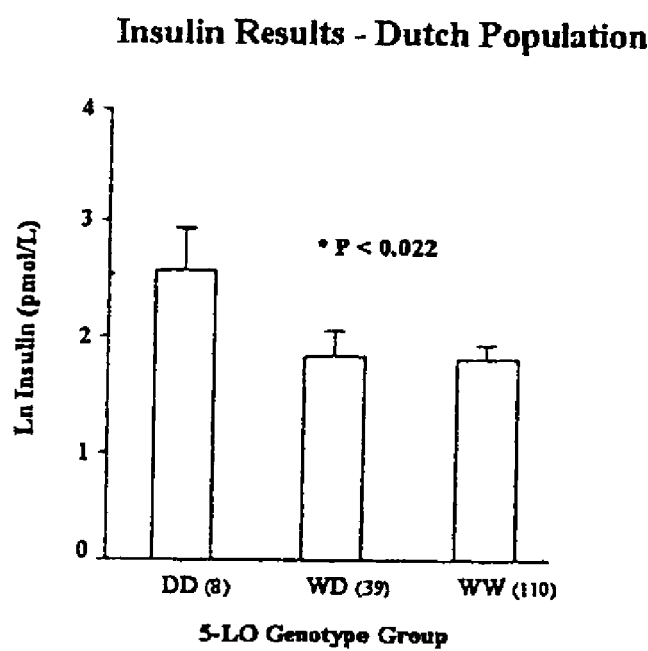
FIG. 9 is a graph depicting the correlation of 5-LO promoter genotypes with insulin levels.
Figure 10:
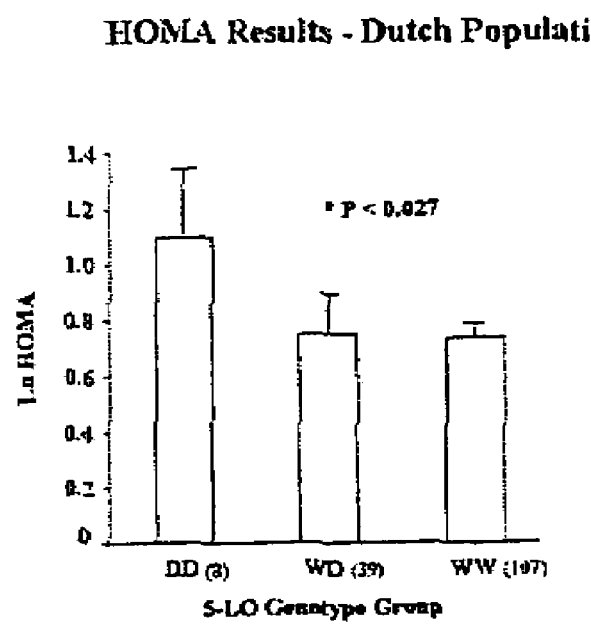
FIG. 10 is a graph depicting the correlation of 5-LO genotypes with insulin resistance.

The deleted alleles also lead to significantly higher fasting insulin levels (FIG. 9) as well as insulin resistance (HOMA analysis; FIG. 10), both of which are known risk factors for diabetes. Taken together, these results strongly suggest that genetic variation in the 5LO gene contributes to CAD-related traits in the human population, with deleted alleles predisposing individuals to CAD and diabetes. Given the importance and frequency of CAD in the US and other Western societies, we believe that identification of individuals who are carriers of deleted alleles would serve as a beneficial and powerful screening test in the general population or for those who are already at risk of developing CAD.

We have developed a method that can be used as a diagnostic DNA test to determine the form of the 5LO gene that an individual has. PCR is used to amplify a portion of the 5LO gene from an individual. Based on the size of this amplified fragment, it is possible to determine whether an individual carries the normal form (wildtype allele) or a variant version (deleted allele) of the 5LO gene. There are currently no genetic tests available for common forms of CAD or diabetes, which by far accounts for most of the heart attacks that individuals suffer. Given the importance and prevalence of CAD and diabetes, we believe that this is the first such test that can be widely used to identify at-risk individuals in the population.

It is evident that subject invention provides a convenient and effective way of determining whether a patient will be susceptible to atherosclerosis and hyperglycemic disease. The subject methods will provide a number of benefits, including preventive treatment and diet. As such, the subject invention represents a significant contribution to the art.

Example 3

Eicosanoids are lipid mediators of inflammation and hypersensitivity reactions, and arachidonate 5-lipoxygenase (5-LO or ALOX5) is the key enzyme in the oxidative biosynthesis of a class of paracrine and autocrine eicosanoids known as leukotrienes. The dihydroxy leukotriene B4 is a potent leukocyte chemoattractant, while the cysteinyl leukotrienes increase vascular permeability and contract vascular smooth muscle. The cysteinyl leukotrienes have been linked to asthma, and 5-lipoxygenase promoter genotypes interact strongly with effects of 5-lipoxygenase inhibition among asthmatics.

Atherosclerosis is a chronic inflammatory process involving recruitment and accumulation of monocytes/macrophages and dendritic cells in artery walls where they become loaded with modified and aggregated low density lipoproteins. Molecular determinants of the pathologic chronicity of this process are unknown. Variation in the Dwyer: Atherosclerosis and 5-LO 4.5-lipoxygenase promoter may alter eicosanoid-mediated inflammatory circuits in the artery wall and promote atherogenesis.

Methods

Cohort. The cohort of 573 women and men, aged 45 to 60 and 40 to 60 years, respectively, were free of diagnosed cardiovascular disease when randomly sampled from an employee population. Hispanics and smokers were over sampled, and the participation rate was 85 percent. Baseline examinations in 1995–96 were followed by two examinations at 1.5 yr intervals where buffy coat for DNA extraction was collected (n=500). This group included non-Hispanic whites (55.1 percent), Hispanics (29.6), Asian/Pacific Islanders (7.7), African Americans (5.3) and other groups (2.3). Study protocol and informed consent were approved by the Institutional Review Board of the Keck School of Medicine.

Carotid intima-media thickness (IMT). Atherosclerosis in the posterior wall of the common carotid arteries was estimated in the baseline examination as bilateral intima-media thickness (IMT) by high-resolution B-mode ultrasound, as described previously. The coefficient of variation was 2.8% for repeated scans by different sonographers.

Genotyping. DNA was isolated from 500 participants, and the number of tandem Sp1 binding motifs (5'-GGGCGG-3') in the 5-lipoxygenase (ALOX5) promoter was determined in 470 participants according to previously described methods. Genotype for 30 specimens could not be determined due to PCR failure. The resulting six alleles had relative frequencies of 2.9, 13.1, 80.5, 2.8, 0.5 and 0.2 percent (n=940) for 3 to 8 tandem Sp1 motifs, respectively. Variant alleles involved deletions (1 or 2) or additions (1 to 3) of Sp 1 motifs relative to the five tandem motifs in the common (wild type) allele.

The distribution of genotypes did not significantly deviate from that expected by random combination of variant and common alleles within any of the race/ethnic groups ($P \geq 0.05$, Hardy-Weinberg equilibrium $X^2$).

Statistical analysis. Adjusted means and P-values for differences between genotype groups were estimated at the mean value of covariates by least squares regression. Relative odds of elevated intima-media thickness were estimated by ordinal logistic regression using deciles of intima-media thickness as the ordinal outcome. Covariates in statistical models relating intima-media thickness to genotype were (Model 1) age, interaction of genotype with age (centered at age 50), sex, body height, race/ethnicity; (Model 2, behavior) plus cigarette smoking status (current/former/never), physical activity, dietary intake of saturated fat (percent energy), and intake of alcohol; (Model 3, biological) plus serum cholesterol, serum HDL cholesterol, systolic blood pressure, body mass index ($kg/m^2$), history of diabetes (type 1 or 2), use of anti-hypertensive medication, and use of lipid lowering medication.

The primary analyses compared carriers of the common allele with non-carriers (variants). This categorization was derived from a pharmacogenetic interaction involving these two genotype groups. Some a posteriori comparisons for additional 5-lipoxygenase genotype sub-groups are also presented for hypothesis generation.

Results

Genotyping yielded 442 carriers of the 5-lipoxygenase common allele and 28 (6.0 percent) non-carriers (variants). Major cardiovascular risk factors are presented for the cohort by promoter genotype in Table 3. No large differences between carriers and variants were apparent. However, race/ethnicity groups did differ in the prevalence of variant genotypes (P<0.001).

TABLE 3

Major cardiovascular risk factors by 5-lipoxygenase genotype group (carriers and non-carriers of the common allele).

| Variable | Carriers (n = 442) | | Variants (n = 28) | | P-value |
|---|---|---|---|---|---|
| | mean | SD | mean | SD | |
| age (yr) | 50.0 | 4.6 | 49.3 | 4.8 | 0.46 |
| systolic blood pressure (mmHg) | 128 | 16 | 132 | 14 | 0.16 |
| serum cholesterol (mg/dL) | 215 | 28 | 207 | 37 | 0.26 |
| HDL cholesterol (mg/dL) | 57 | 12 | 54 | 14 | 0.22 |

TABLE 3-continued

Major cardiovascular risk factors by 5-lipoxygenase genotype group (carriers and non-carriers of the common allele).

| Variable | Carriers (n = 442) | | Variants (n = 28) | | P-value |
|---|---|---|---|---|---|
| | percent | SD | percent | SD | |
| sex (female) | 46.8 | | 42.9 | | 0.68 |
| current smoking | 24.2 | | 21.4 | | 0.74 |
| former smoking | 26.5 | | 25.0 | | 0.86 |

Note.
Carriers denotes carriers of the common 5-lipoxygenase allele (5 tandem Sp1 motifs) and Variants denotes non-carriers of the common allele. SD is standard deviation and the P-value is for the difference between Carriers and Variants (t-test for continuous variables, chi-square for categorical).

5-lipoxycenase Polymorphism and Atherosclerosis.

Means and medians of carotid intima-media thickness by 5-lipoxygenase genotype are presented in Table 2. The significance level of the unadjusted elevation of intima-media thickness in the variant group was confirmed by nonparametric bootstrap analysis. After adjustment for age, sex, body height and race/ethnicity, mean (±Standard Error) intima-media thickness was elevated by 80±19 μm in the variants relative to carriers of the common allele (P<0.001; Table 4). This elevation remained significant after adjustment for behavioral risk factors (78±19 μm, P<0.001) and biologic confounders or mediators and preventive treatments (62±17 μm, P<0.001). The magnitude of the apparent genotype effect in this last model is comparable to that for diabetes in this cohort (64±26 μm), and larger than that for current smoking (45±11 μm).

TABLE 4

Carotid intima-media thickness (IMT) by 5-lipoxygenase genotype group.

| | intima-media thickness (μm) | | |
|---|---|---|---|
| | Carriers (n = 442) | Variants (n = 28) | P-value |
| No covariates | | | |
| mean (standard deviation) | 661 (95) | 736 (141) | <0.001 |
| Bootstrap P-value | | | <0.001 |
| median (Kruskal-Wallis) | 641 | 725 | 0.004 |
| minimum | 428 | 526 | |
| maximum | 1096 | 1076 | |
| Multivariate[1] | | | |
| mean ± Standard Error | 661 ± 4 | 740 ± 18 | <0.001 |
| Multivariate[2] | | | |
| mean ± Standard Error | 661 ± 4 | 739 ± 18 | <0.001 |
| Multivariate[3] | | | |
| mean ± Standard Error | 662 ± 4 | 724 ± 16 | <0.001 |

[1]Covariates were age, sex, body height and race/ethnicity (non-Hispanic white, Hispanic, Asian/Pacific Islander, African American, other).
[2]Additional covariates were behavioral risk factors (smoking, physical activity, dietary saturated fat, and intake of alcohol).

Figure 11:
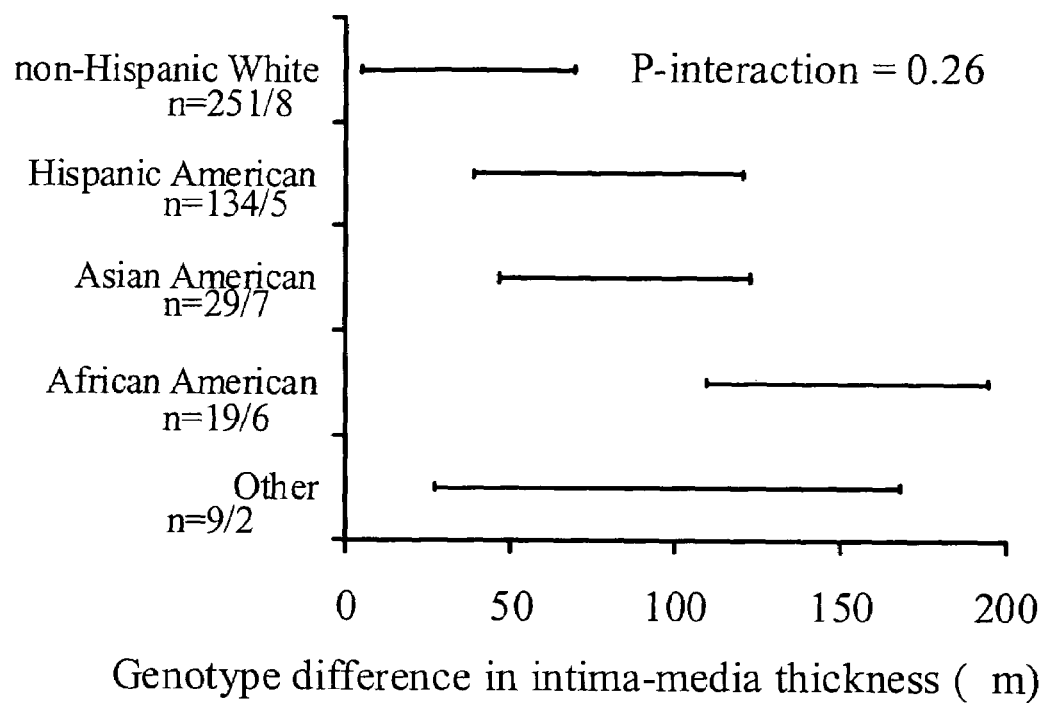
FIG. 11. Difference between intima-media thickness of the variant 5-lipoxygenase group and carriers of the common allele by race/ethnicity (error bars indicate standard error). Means were adjusted for age, sex and body height. Sample sizes are for carriers/variants within each race/ethnic group. The percent of variant genotypes in each race/ethnicity group was 3.1 (non-Hispanic white), 3.6 (Hispanic), 19.4 (Asian/Pacific Islander), 24.0 (African American) and 18.2 (other).

This apparent atherogenic effect did not significantly interact with sex, race/ethnicity or smoking status, but did increase with age (P-interaction=0.04). Given the race/ethnicity differences in genotype prevalence, the apparent effect of the variant genotypes was estimated within each group (FIG. 11). The relative magnitude of this 5-lipoxygenase genotype association was estimated with ordinal logistic regression. After adjustment for age, sex, height and race/ethnicity, the odds of increased wall thickness were increased 4-fold in the variants relative to carriers (odds ratio=4.1, 95% confidence interval=2.1 to 8.2; P<0.001). Adjustment for numerous potential confounders did not attenuate this relation appreciably. (OR=3.7, P<0.001).

Figure 12:
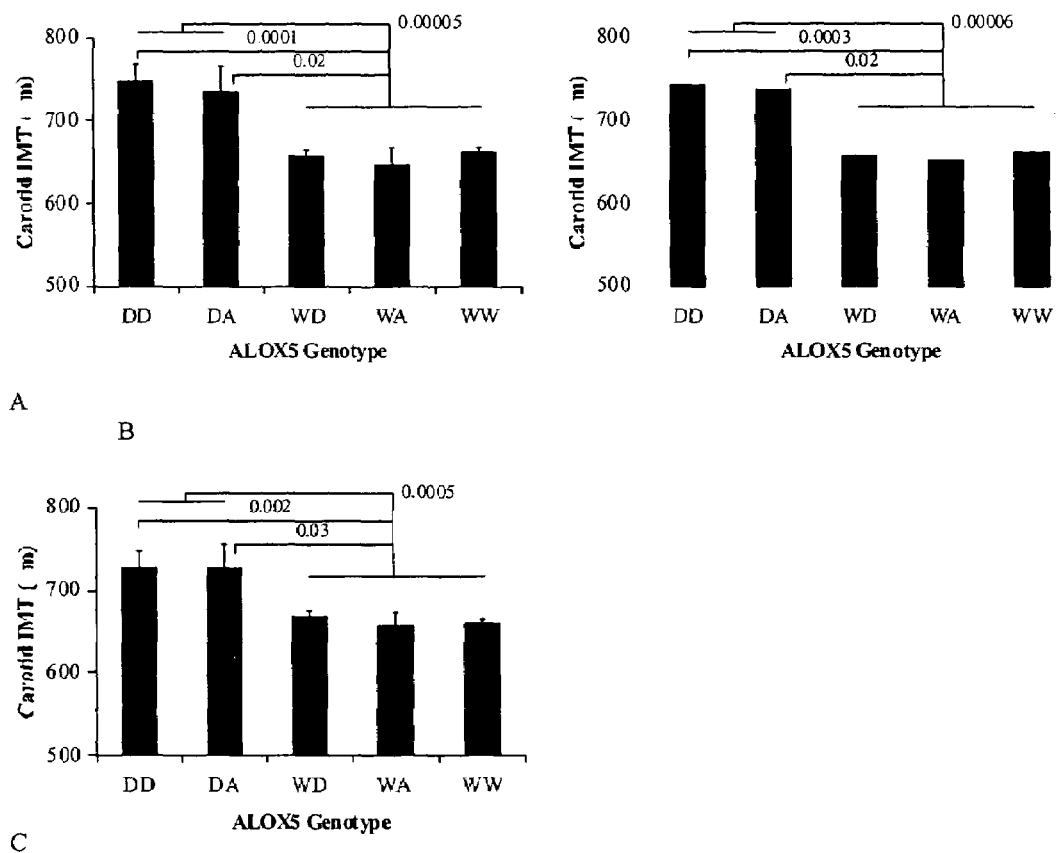
FIG. 12. Carotid intima-media thickness (IMT) by five 5-lipoxygenase (ALOX5) genotype groups. Panel A was adjusted for age, sex, body height and race/ethnicity. Panel B was also adjusted for behavioral risk factors (smoking status, physical activity, dietary saturated fat, and intake of alcohol). Panel C was also adjusted for biological risk factors and preventive pharmacologic treatment (serum cholesterol, serum HDL cholesterol, systolic blood pressure, body mass index, diabetes, anti-hypertensive medication, and lipid lowering medication). D=deletion alleles, A=addition alleles, W=common allele (5 tandem Sp1 binding motifs). P-values are for differences between indicated genotypes, and error bars indicate standard errors.

Genotype differences in intima-media thickness were further investigated across five 5-lipoxygenase groups derived from combinations of common (W), deletion (D) and addition (A) alleles: DD (n=18), DA (n=9), WD (n=105), WA (n=22) and WW (n=315). The M genotype was observed in only one person (intima-media thickness=661 μm). Differences between the five genotype groups confirmed a recessive pattern of effects (FIG. 12).

While data on the 5-lipoxygenase pathway and atherosclerosis are limited, available evidence from two animal studies and a human histology study is consistent with an atherogenic effect of increased leukotriene production. Atherosclerosis in the aortic arch was almost absent from susceptible mice carrying one null 5-lipoxygenase allele relative to carriers of two functional alleles, suggesting that this inflammatory pathway is necessary in atherosclerosis. In a second study, foam cell formation was reduced in three strains of atherosclerosis-susceptible mice treated with a leukotriene B4 receptor antagonist. Third, a recent histology study found an abundance of 5-lipoxygenase (but not 15-lipoxygenase) in macrophages/foam cells, dendritic cells and artery wall cells from human atherosclerotic lesions.

Combining these findings with recent studies of leukotriene receptors expressed by endothelial cells and macrophages, a model of leukotriene-mediated vascular inflammation in atherosclerosis is proposed. In this model, leukotrienes produced by macrophages and dendritic cells in the artery wall have autocrine effects and paracrine effects on endothelial cells, lymphocytes, smooth muscle cells and other macrophages/dendritic cells. Upregulation of this "inflammatory circuit" by environmental or genetic factors would promote atherosclerosis by enhancing known effects of leukotrienes on leukocyte recruitment, endothelial cell dysfunction, intimal edema, smooth muscle cell proliferation and immune reactivity. This model provides a mechanism whereby increased gene expression among 5-lipoxygenase variant genotypes would lead to our finding of increased carotid intima-media thickness in this group and are consistent with a hypothesis of increased leukotriene production among promoter variants.

The above data demonstrate that genetic variation in an inflammatory pathway, and the leukotriene pathway in particular, can trigger atherogenesis in humans. These findings can lead to new dietary and targeted molecular approaches to prevention and treatment of cardiovascular disease by genotype, with particular application to populations of non-European descent.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

SEQUENCE LISTING

```
<160> NUMBER OF SEQ ID NOS: 18

<210> SEQ ID NO 1
<211> LENGTH: 2497
<212> TYPE: DNA
<213> ORGANISM: H. sapiens
<220> FEATURE:
<221> NAME/KEY: CDS
<222> LOCATION: (45)...(2069)
<223> OTHER INFORMATION: Wild-type 5LO coding sequence

<400> SEQUENCE: 1
gggcgccgag gctcccccgcc gctcgctgct ccccggcccg cgcc atg ccc tcc tac        56
                                                 Met Pro Ser Tyr
                                                  1 acg gtc acc gtg gcc act ggc agc cag tgg ttc gcc ggc act gac gac         104
Thr Val Thr Val Ala Thr Gly Ser Gln Trp Phe Ala Gly Thr Asp Asp
  5                  10                  15                  20 tac atc tac ctc agc ctc gtg ggc tcg gcg ggc tgc agc gag aag cac         152
Tyr Ile Tyr Leu Ser Leu Val Gly Ser Ala Gly Cys Ser Glu Lys His
             25                  30                  35 ctg ctg gac aag ccc ttc tac aac gac ttc gag cgt ggc gcg gtg gat         200
Leu Leu Asp Lys Pro Phe Tyr Asn Asp Phe Glu Arg Gly Ala Val Asp
         40                  45                  50 tca tac gac gtg act gtg gac gag gaa ctg ggc gag atc cag ctg gtc         248
Ser Tyr Asp Val Thr Val Asp Glu Glu Leu Gly Glu Ile Gln Leu Val
```

```
                  55                  60                  65
aga atc gag aag cgc aag tac tgg ctg aat gac gac tgg tac ctg aag         296
Arg Ile Glu Lys Arg Lys Tyr Trp Leu Asn Asp Asp Trp Tyr Leu Lys
            70                  75                  80 tac atc acg ctg aag acg ccc cac ggg gac tac atc gag ttc ccc tgc         344
Tyr Ile Thr Leu Lys Thr Pro His Gly Asp Tyr Ile Glu Phe Pro Cys
85              90                  95                  100 tac cgc tgg atc acc ggc gat gtc gag gtt gtc ctg agg gat gga cgc         392
Tyr Arg Trp Ile Thr Gly Asp Val Glu Val Val Leu Arg Asp Gly Arg
                    105                 110                 115 gca aag ttg gcc cga gat gac caa att cac att ctc aag caa cac cga         440
Ala Lys Leu Ala Arg Asp Asp Gln Ile His Ile Leu Lys Gln His Arg
                120                 125                 130 cgt aaa gaa ctg gaa aca cgg caa aaa caa tat cga tgg atg gag tgg         488
Arg Lys Glu Leu Glu Thr Arg Gln Lys Gln Tyr Arg Trp Met Glu Trp
            135                 140                 145 aac cct ggc ttc ccc ttg agc atc gat gcc aaa tgc cac aag gat tta         536
Asn Pro Gly Phe Pro Leu Ser Ile Asp Ala Lys Cys His Lys Asp Leu
        150                 155                 160 ccc cgt gat atc cag ttt gat agt gaa aaa gga gtg gac ttt gtt ctg         584
Pro Arg Asp Ile Gln Phe Asp Ser Glu Lys Gly Val Asp Phe Val Leu
165                 170                 175                 180 aat tac tcc aaa gcg atg gag aac ctg ttc atc aac cgc ttc atg cac         632
Asn Tyr Ser Lys Ala Met Glu Asn Leu Phe Ile Asn Arg Phe Met His
                185                 190                 195 atg ttc cag tct tct tgg aat gac ttc gcc gac ttt gag aaa atc ttt         680
Met Phe Gln Ser Ser Trp Asn Asp Phe Ala Asp Phe Glu Lys Ile Phe
                200                 205                 210 gtc aag atc agc aac act att tct gag cgg gtc atg aat cac tgg cag         728
Val Lys Ile Ser Asn Thr Ile Ser Glu Arg Val Met Asn His Trp Gln
            215                 220                 225 gaa gac ctg atg ttt ggc tac cag ttc ctg aat ggc tgc aac cct gtg         776
Glu Asp Leu Met Phe Gly Tyr Gln Phe Leu Asn Gly Cys Asn Pro Val
        230                 235                 240 ttg atc cgg cgc tgc aca gag ctg ccc gag aag ctc ccg gtg acc acg         824
Leu Ile Arg Arg Cys Thr Glu Leu Pro Glu Lys Leu Pro Val Thr Thr
245                 250                 255                 260 gag atg gta gag tgc agc ctg gag cgg cag ctc agc ttg gag cag gag         872
Glu Met Val Glu Cys Ser Leu Glu Arg Gln Leu Ser Leu Glu Gln Glu
                265                 270                 275 gtc cag caa ggg aac att ttc atc gtg gac ttt gag ctg ctg gat ggc         920
Val Gln Gln Gly Asn Ile Phe Ile Val Asp Phe Glu Leu Leu Asp Gly
                280                 285                 290 atc gat gcc aac aaa aca gac ccc tgc aca ctc cag ttc ctg gcc gct         968
Ile Asp Ala Asn Lys Thr Asp Pro Cys Thr Leu Gln Phe Leu Ala Ala
            295                 300                 305 ccc atc tgc ttg ctg tat aag aac ctg gcc aac aag att gtc ccc att        1016
Pro Ile Cys Leu Leu Tyr Lys Asn Leu Ala Asn Lys Ile Val Pro Ile
        310                 315                 320 gcc atc cag ctc aac caa atc ccg gga gat gag aac cct att ttc ctc        1064
Ala Ile Gln Leu Asn Gln Ile Pro Gly Asp Glu Asn Pro Ile Phe Leu
325                 330                 335                 340 cct tcg gat gca aaa tac gac tgg ctt ttg gcc aaa atc tgg gtg cgt        1112
Pro Ser Asp Ala Lys Tyr Asp Trp Leu Leu Ala Lys Ile Trp Val Arg
                345                 350                 355 tcc agt gac ttc cac gtc cac cag acc atc acc cac ctt ctg cga aca        1160
Ser Ser Asp Phe His Val His Gln Thr Ile Thr His Leu Leu Arg Thr
                360                 365                 370 cat ctg gtg tct gag gtt ttt ggc att gca atg tac cgc cag ctg cct        1208
```

```
                His Leu Val Ser Glu Val Phe Gly Ile Ala Met Tyr Arg Gln Leu Pro
                            375                 380                 385 gct gtg cac ccc att ttc aag ctg ctg gtg gca cac gtg aga ttc acc        1256
Ala Val His Pro Ile Phe Lys Leu Leu Val Ala His Val Arg Phe Thr
390                 395                 400 att gca atc aac acc aag gcc cgt gag cag ctc atc tgc gag tgt ggc        1304
Ile Ala Ile Asn Thr Lys Ala Arg Glu Gln Leu Ile Cys Glu Cys Gly
405                 410                 415                 420 ctc ttt gac aag gcc aac gcc aca ggg ggc ggt ggg cac gtg cag atg        1352
Leu Phe Asp Lys Ala Asn Ala Thr Gly Gly Gly Gly His Val Gln Met
                425                 430                 435 gtg cag agg gcc atg aag gac ctg acc tat gcc tcc ctg tgc ttt ccc        1400
Val Gln Arg Ala Met Lys Asp Leu Thr Tyr Ala Ser Leu Cys Phe Pro
                440                 445                 450 gag gcc atc aag gcc cgg ggc atg gag agc aaa gaa gac atc ccc tac        1448
Glu Ala Ile Lys Ala Arg Gly Met Glu Ser Lys Glu Asp Ile Pro Tyr
                455                 460                 465 tac ttc tac cgg gac gac ggg ctc ctg gtg tgg gaa gcc atc agg acg        1496
Tyr Phe Tyr Arg Asp Asp Gly Leu Leu Val Trp Glu Ala Ile Arg Thr
            470                 475                 480 ttc acg gcc gag gtg gta gac atc tac tac gag ggc gac cag gtg gtg        1544
Phe Thr Ala Glu Val Val Asp Ile Tyr Tyr Glu Gly Asp Gln Val Val
485                 490                 495                 500 gag gag gac ccg gag ctg cag gac ttc gtg aac gat gtc tac gtg tac        1592
Glu Glu Asp Pro Glu Leu Gln Asp Phe Val Asn Asp Val Tyr Val Tyr
                505                 510                 515 ggc atg cgg ggc cgc aag tcc tca ggc ttc ccc aag tcg gtc aag agc        1640
Gly Met Arg Gly Arg Lys Ser Ser Gly Phe Pro Lys Ser Val Lys Ser
                520                 525                 530 cgg gag cag ctg tcg gag tac ctg acc gtg gtg atc ttc acc gcc tcc        1688
Arg Glu Gln Leu Ser Glu Tyr Leu Thr Val Val Ile Phe Thr Ala Ser
                535                 540                 545 gcc cag cac gcc gcg gtc aac ttc ggc cag tac gac tgg tgc tcc tgg        1736
Ala Gln His Ala Ala Val Asn Phe Gly Gln Tyr Asp Trp Cys Ser Trp
                550                 555                 560 atc ccc aat gcg ccc cca acc atg cga gcc ccg cca ccg act gcc aag        1784
Ile Pro Asn Ala Pro Pro Thr Met Arg Ala Pro Pro Pro Thr Ala Lys
565                 570                 575                 580 ggc gtg gtg acc att gag cag atc gtg gac acg ctg ccc gac cgc ggc        1832
Gly Val Val Thr Ile Glu Gln Ile Val Asp Thr Leu Pro Asp Arg Gly
                585                 590                 595 cgc tcc tgc tgg cat ctg ggt gca gtg tgg gcg ctg agc cag ttc cag        1880
Arg Ser Cys Trp His Leu Gly Ala Val Trp Ala Leu Ser Gln Phe Gln
                600                 605                 610 gaa aac gag ctg ttc ctg ggc atg tac cca gaa gag cat ttt atc gag        1928
Glu Asn Glu Leu Phe Leu Gly Met Tyr Pro Glu Glu His Phe Ile Glu
                615                 620                 625 aag cct gtg aag gaa gcc atg gcc cga ttc cgc aag aac ctc gag gcc        1976
Lys Pro Val Lys Glu Ala Met Ala Arg Phe Arg Lys Asn Leu Glu Ala
                630                 635                 640 att gtc agc gtg att gct gag cgc aac aag aag aag cag ctg cca tat        2024
Ile Val Ser Val Ile Ala Glu Arg Asn Lys Lys Lys Gln Leu Pro Tyr
645                 650                 655                 660 tac tac ttg tcc cca gac cgg att ccg aac agt gtg gcc atc tga            2069
Tyr Tyr Leu Ser Pro Asp Arg Ile Pro Asn Ser Val Ala Ile *
                665                 670 gcacactgcc agtctcactg tgggaaggcc agctgcccca gccagatgga ctccagcctg      2129
cctggcaggc tgtctggcca ggcctcttgg cagtcacatc tcttcctccg aggccagtac      2189
```

-continued

| | |
|---|---|
| ctttccattt attctttgat cttcagggaa ctgcatagat tgtatcaaag tgtaaacacc | 2249 |
| atagggaccc attctacaca gagcaggact gcacaggcgt cctgtccaca cccagctcag | 2309 |
| catttccaca ccaagcagca acagcaaatc acgaccactg atagatgtct attcttgttg | 2369 |
| gagacatggg atgattattt tctgttctat ttgtgcttag tccaattcct tgcacatagt | 2429 |
| aggtacccaa ttcaattact attgaatgaa ttaagaattg gttgccataa aaataaatca | 2489 |
| gttcattt | 2497 |

<210> SEQ ID NO 2
<211> LENGTH: 20
<212> TYPE: DNA
<213> ORGANISM: M. musculus
<400> SEQUENCE: 2
atcgccttct tgacgagttc                                          20

<210> SEQ ID NO 3
<211> LENGTH: 21
<212> TYPE: DNA
<213> ORGANISM: M. musculus
<400> SEQUENCE: 3
gcaggaagtg gctactgtgg a                                        21

<210> SEQ ID NO 4
<211> LENGTH: 21
<212> TYPE: DNA
<213> ORGANISM: M. musculus
<400> SEQUENCE: 4
tgcaacccag tactcatcaa g                                        21

<210> SEQ ID NO 5
<211> LENGTH: 25
<212> TYPE: DNA
<213> ORGANISM: M. musculus
<400> SEQUENCE: 5
accccaagac gtgctcccag gatga                                    25

<210> SEQ ID NO 6
<211> LENGTH: 24
<212> TYPE: DNA
<213> ORGANISM: M. musculus
<400> SEQUENCE: 6
cgcagtgctc ctcatctgac ttgt                                     24

<210> SEQ ID NO 7
<211> LENGTH: 25
<212> TYPE: DNA
<213> ORGANISM: M. musculus
<400> SEQUENCE: 7
aggatctcgt cgtgacccat ggcga                                    25

<210> SEQ ID NO 8
<211> LENGTH: 26
<212> TYPE: DNA
<213> ORGANISM: M. musculus
<400> SEQUENCE: 8

```
gagcggcgat accgtaaagc acgagg                                      26

<210> SEQ ID NO 9
<211> LENGTH: 27
<212> TYPE: DNA
<213> ORGANISM: M. musculus

<400> SEQUENCE: 9
atgccctatg ccctcctaca ctgtcac                                     27

<210> SEQ ID NO 10
<211> LENGTH: 21
<212> TYPE: DNA
<213> ORGANISM: M. musculus

<400> SEQUENCE: 10
ccactccatc catctatact g                                           21

<210> SEQ ID NO 11
<211> LENGTH: 22
<212> TYPE: DNA
<213> ORGANISM: M. musculus

<400> SEQUENCE: 11
gcagcacaga cgtaaagaac tg                                          22

<210> SEQ ID NO 12
<211> LENGTH: 21
<212> TYPE: DNA
<213> ORGANISM: M. musculus

<400> SEQUENCE: 12
gaggaagtca ctggaacgca c                                           21

<210> SEQ ID NO 13
<211> LENGTH: 22
<212> TYPE: DNA
<213> ORGANISM: M. musculus

<400> SEQUENCE: 13
ctacggattc aaagtacgac tg                                          22

<210> SEQ ID NO 14
<211> LENGTH: 21
<212> TYPE: DNA
<213> ORGANISM: M. musculus

<400> SEQUENCE: 14
caggtactcg gacagcttct c                                           21

<210> SEQ ID NO 15
<211> LENGTH: 21
<212> TYPE: DNA
<213> ORGANISM: M. musculus

<400> SEQUENCE: 15
gctatccagt cgttcacgat g                                           21

<210> SEQ ID NO 16
<211> LENGTH: 21
<212> TYPE: DNA
<213> ORGANISM: M. musculus
```

<400> SEQUENCE: 16
gcagcacttc gagcttggaa g                                           21

<210> SEQ ID NO 17
<211> LENGTH: 2107
<212> TYPE: DNA
<213> ORGANISM: M. musculus
<220> FEATURE:
<221> NAME/KEY: CDS
<222> LOCATION: (83)...(2107)
<223> OTHER INFORMATION: CAST strain of mouse, coding sequence
<220> FEATURE:
<221> NAME/KEY: misc_feature
<222> LOCATION: (1)...(2107)
<223> OTHER INFORMATION: n = A,T,C or G

<400> SEQUENCE: 17
agggtcaana agttggtggg ctgccacgcc gagcttcgcg ggctcntgcg cccacgccag        60
cagcactcac ttgcccggtg tc atg ccc tcc tac acg gtc acc gtg gcc acc       112
                         Met Pro Ser Tyr Thr Val Thr Val Ala Thr
                          1               5                  10 ggc agc cag tgg ttc gcg ggc acc gac gac tac atc tac ctc agc ctc        160
Gly Ser Gln Trp Phe Ala Gly Thr Asp Asp Tyr Ile Tyr Leu Ser Leu
             15                  20                  25 att ggc tct gcg ggc tgt agc gag aag cat ctg ctg gac aag gca ttc        208
Ile Gly Ser Ala Gly Cys Ser Glu Lys His Leu Leu Asp Lys Ala Phe
         30                  35                  40 tac aat gac ttc gaa cgt ggc gcg gtg gac tcc tac gat gtc act gtg        256
Tyr Asn Asp Phe Glu Arg Gly Ala Val Asp Ser Tyr Asp Val Thr Val
     45                  50                  55 gat gag gag ctg ggc gag atc tac cta gtc aaa att gag aag cgc aaa        304
Asp Glu Glu Leu Gly Glu Ile Tyr Leu Val Lys Ile Glu Lys Arg Lys
 60                  65                  70 tac tgg ctc cat gat gac tgg tac ctg aag tac atc aca ctg aag aca        352
Tyr Trp Leu His Asp Asp Trp Tyr Leu Lys Tyr Ile Thr Leu Lys Thr
 75                  80                  85                  90 ccc cac ggg gac tac atc gag ttc cca tgt tac cgc tgg atc aca ggc        400
Pro His Gly Asp Tyr Ile Glu Phe Pro Cys Tyr Arg Trp Ile Thr Gly
                 95                 100                 105 gag ggc gag att gtc ctg agg gat gga cgt gca aaa ttg gcc cga gat        448
Glu Gly Glu Ile Val Leu Arg Asp Gly Arg Ala Lys Leu Ala Arg Asp
            110                 115                 120 gac caa att cac atc ctc aag cag cac aga cgt aaa gaa ctg gag gca        496
Asp Gln Ile His Ile Leu Lys Gln His Arg Arg Lys Glu Leu Glu Ala
        125                 130                 135 cgg caa aaa cag tat cga tgg atg gag tgg aac ccc ggc ttc cct ttg        544
Arg Gln Lys Gln Tyr Arg Trp Met Glu Trp Asn Pro Gly Phe Pro Leu
    140                 145                 150 agt atc gat gcc aaa tgc cac aag gat ctg ccc cga gat atc cag ttt        592
Ser Ile Asp Ala Lys Cys His Lys Asp Leu Pro Arg Asp Ile Gln Phe
155                 160                 165                 170 gat agt gaa aaa gga gtg gac ttt gtt ctg aac tac tca aaa gcg atg        640
Asp Ser Glu Lys Gly Val Asp Phe Val Leu Asn Tyr Ser Lys Ala Met
                175                 180                 185 gag aac ctg ttc atc aac cgc ttc atg cac atg ttc cag tct tcc tgg        688
Glu Asn Leu Phe Ile Asn Arg Phe Met His Met Phe Gln Ser Ser Trp
            190                 195                 200 cac gac ttt gct gac ttt gag aaa atc ttc gtc aaa atc agc aac act        736
His Asp Phe Ala Asp Phe Glu Lys Ile Phe Val Lys Ile Ser Asn Thr
        205                 210                 215 ata tct gag cga gtc aag aac cac tgg cag gaa gac ctc atg ttt ggc        784

```
                Ile Ser Glu Arg Val Lys Asn His Trp Gln Glu Asp Leu Met Phe Gly
                    220                 225                 230 tac cag ttc ctg aat ggc tgc aac cca gta ctc atc aag cgc tgc aca              832
Tyr Gln Phe Leu Asn Gly Cys Asn Pro Val Leu Ile Lys Arg Cys Thr
235                 240                 245                 250 gcg ttg ccc ccg aag ctc cca gtg acc aca gag atg gtg gag tgc agc              880
Ala Leu Pro Pro Lys Leu Pro Val Thr Thr Glu Met Val Glu Cys Ser
                    255                 260                 265 cta gag cgg cag ctc agt tta gaa cag gaa gta cag gaa ggg aac att              928
Leu Glu Arg Gln Leu Ser Leu Glu Gln Glu Val Gln Glu Gly Asn Ile
                270                 275                 280 ttc atc gtt gat tac gag cta ctg gat ggc atc gat gct aac aaa act              976
Phe Ile Val Asp Tyr Glu Leu Leu Asp Gly Ile Asp Ala Asn Lys Thr
            285                 290                 295 gac ccc tgt aca cac cag ttc ctg gct gcc ccc atc tgc ctg cta tat             1024
Asp Pro Cys Thr His Gln Phe Leu Ala Ala Pro Ile Cys Leu Leu Tyr
        300                 305                 310 aag aac cta gcc aac aag att gtt ccc att gcc atc cag ctc aac caa             1072
Lys Asn Leu Ala Asn Lys Ile Val Pro Ile Ala Ile Gln Leu Asn Gln
315                 320                 325                 330 acc cct gga gag agt aac cca atc ttc ctc cct acg gat tca aag tac             1120
Thr Pro Gly Glu Ser Asn Pro Ile Phe Leu Pro Thr Asp Ser Lys Tyr
                    335                 340                 345 gac tgg ctt ttg gcc aaa atc tgg gtg cgt tcc agt gac ttc cac gtc             1168
Asp Trp Leu Leu Ala Lys Ile Trp Val Arg Ser Ser Asp Phe His Val
                350                 355                 360 cat caa acg atc acc cac ctt ctg cgc acg cat ctg gtg tct gag gtg             1216
His Gln Thr Ile Thr His Leu Leu Arg Thr His Leu Val Ser Glu Val
            365                 370                 375 ttt ggt atc gcc atg tac cgc cag ctg cct gct gtg cat ccc ctt ttc             1264
Phe Gly Ile Ala Met Tyr Arg Gln Leu Pro Ala Val His Pro Leu Phe
        380                 385                 390 aag ctg ctg gta gcc cat gtg agg ttc acc att gct atc aac act aag             1312
Lys Leu Leu Val Ala His Val Arg Phe Thr Ile Ala Ile Asn Thr Lys
395                 400                 405                 410 gcc cgg gaa cag ctt atc tgc gag tat ggc ctt ttt gac aag gcc aat             1360
Ala Arg Glu Gln Leu Ile Cys Glu Tyr Gly Leu Phe Asp Lys Ala Asn
                    415                 420                 425 gcc acc ggg ggt gga ggg cac gtg cag atg gtg cag agg gct gtc cag             1408
Ala Thr Gly Gly Gly Gly His Val Gln Met Val Gln Arg Ala Val Gln
                430                 435                 440 gat ctg acc tat tcc tcc ctg tgt ttc ccg gag gcc atc aag gcc cgg             1456
Asp Leu Thr Tyr Ser Ser Leu Cys Phe Pro Glu Ala Ile Lys Ala Arg
            445                 450                 455 ggc atg gac agc acg gaa gac atc ccc ttc tac ttc tat cgt gat gat             1504
Gly Met Asp Ser Thr Glu Asp Ile Pro Phe Tyr Phe Tyr Arg Asp Asp
        460                 465                 470 gga ctg ctc gtg tgg gag gct atc cag tcg ttc aca atg gag gtg gtg             1552
Gly Leu Leu Val Trp Glu Ala Ile Gln Ser Phe Thr Met Glu Val Val
475                 480                 485                 490 agc atc tac tat gag aac gac cag gtg gtg gag gag gac cag gaa ctg             1600
Ser Ile Tyr Tyr Glu Asn Asp Gln Val Val Glu Glu Asp Gln Glu Leu
                    495                 500                 505 cag gac ttc gtg aag gat gtt tac gtg tac ggc atg cgg ggc aaa aag             1648
Gln Asp Phe Val Lys Asp Val Tyr Val Tyr Gly Met Arg Gly Lys Lys
                510                 515                 520 gcc tca ggt ttc ccc aag tcc atc aag agc agg gag aag ctg tcc gag             1696
Ala Ser Gly Phe Pro Lys Ser Ile Lys Ser Arg Glu Lys Leu Ser Glu
            525                 530                 535
```

-continued

```
tac ctg acg gtg gtg atc ttc acg gcc tct gcc cag cat gca gct gta      1744
Tyr Leu Thr Val Val Ile Phe Thr Ala Ser Ala Gln His Ala Ala Val
    540                 545                 550 aac ttc ggc cag tat gac tgg tgc tcc tgg atc ccc aac gct cct cca      1792
Asn Phe Gly Gln Tyr Asp Trp Cys Ser Trp Ile Pro Asn Ala Pro Pro
555                 560                 565                 570 act atg cgg gcc cca cca ccc acg gcc aag ggt gtg gtc acc atc gag      1840
Thr Met Arg Ala Pro Pro Pro Thr Ala Lys Gly Val Val Thr Ile Glu
                575                 580                 585 cag atc gtg gat act cta cca gac cgt ggc cga tca tgt tgg cat cta      1888
Gln Ile Val Asp Thr Leu Pro Asp Arg Gly Arg Ser Cys Trp His Leu
            590                 595                 600 ggt gca gtg tgg gcc ttg agc cag ttt caa gaa aat gag ctg ttt cta      1936
Gly Ala Val Trp Ala Leu Ser Gln Phe Gln Glu Asn Glu Leu Phe Leu
        605                 610                 615 ggc atg tac cca gag gag cat ttc att gag aag cca gtg aag gaa gcc      1984
Gly Met Tyr Pro Glu Glu His Phe Ile Glu Lys Pro Val Lys Glu Ala
620                 625                 630 atg atc cga ttc cgc aag aac ctg gag gcc gtc atc agc gtg atc gcc      2032
Met Ile Arg Phe Arg Lys Asn Leu Glu Ala Val Ile Ser Val Ile Ala
635                 640                 645                 650 gag cgc aat aag aac aaa aag ctc ccc tac tac tac ctg tca cca gac      2080
Glu Arg Asn Lys Asn Lys Lys Leu Pro Tyr Tyr Tyr Leu Ser Pro Asp
                655                 660                 665 agg att ccc aac agt gta gcc atc taa                                   2107
Arg Ile Pro Asn Ser Val Ala Ile *
            670
```

<210> SEQ ID NO 18
<211> LENGTH: 2107
<212> TYPE: DNA
<213> ORGANISM: M. musculus
<220> FEATURE:
<221> NAME/KEY: CDS
<222> LOCATION: (83)...(2107)
<223> OTHER INFORMATION: B6 strain coding sequence

<400> SEQUENCE: 18

```
agggtcaaga agttggtggg ctgccacgcc gagcttcgcg ggctcctgct cccacaccag      60
cagcactcac ttgcccggag tc atg ccc tcc tac acg gtc acc gtg gcc acc     112
                         Met Pro Ser Tyr Thr Val Thr Val Ala Thr
                           1               5                  10 ggc agc cag tgg ttc gcg ggc acc gac gac tac atc tac ctc agc ctc      160
Gly Ser Gln Trp Phe Ala Gly Thr Asp Asp Tyr Ile Tyr Leu Ser Leu
                15                  20                  25 att ggc tct gcg ggc tgt agc gag aag cat ctg ctg gac aag gca ttc      208
Ile Gly Ser Ala Gly Cys Ser Glu Lys His Leu Leu Asp Lys Ala Phe
            30                  35                  40 tac aat gac ttc gaa cgg ggc gcg gtg gac tcc tac gat gtc acc gtg      256
Tyr Asn Asp Phe Glu Arg Gly Ala Val Asp Ser Tyr Asp Val Thr Val
        45                  50                  55 gat gag gag ctg ggc gag atc tac cta gtc aaa att gag aag cgc aaa      304
Asp Glu Glu Leu Gly Glu Ile Tyr Leu Val Lys Ile Glu Lys Arg Lys
    60                  65                  70 tac tgg ctc cat gat gac tgg tac ctg aag tac atc aca ctg aag aca      352
Tyr Trp Leu His Asp Asp Trp Tyr Leu Lys Tyr Ile Thr Leu Lys Thr
75                  80                  85                  90 ccc cac ggg gac tac atc gag ttc cca tgt tac cgc tgg atc aca ggc      400
Pro His Gly Asp Tyr Ile Glu Phe Pro Cys Tyr Arg Trp Ile Thr Gly
                95                 100                 105 gag ggc gag att gtc ctg agg gat gga cgt gca aaa ttg gcc cga gat      448
Glu Gly Glu Ile Val Leu Arg Asp Gly Arg Ala Lys Leu Ala Arg Asp
```

-continued

```
                Glu Gly Glu Ile Val Leu Arg Asp Gly Arg Ala Lys Leu Ala Arg Asp
                            110                 115                 120 gac caa att cac atc ctc aag cag cac aga cgt aaa gaa ctg gag gca        496
Asp Gln Ile His Ile Leu Lys Gln His Arg Arg Lys Glu Leu Glu Ala
            125                 130                 135 cgg caa aaa cag tat aga tgg atg gag tgg aac ccc ggc ttc cct ttg        544
Arg Gln Lys Gln Tyr Arg Trp Met Glu Trp Asn Pro Gly Phe Pro Leu
        140                 145                 150 agt att gat gcc aaa tgc cac aag gat ctg ccc cga gat atc cag ttt        592
Ser Ile Asp Ala Lys Cys His Lys Asp Leu Pro Arg Asp Ile Gln Phe
155                 160                 165                 170 gat agt gaa aaa gga gtg gac ttt gtt ctg aac tac tca aaa gcg atg        640
Asp Ser Glu Lys Gly Val Asp Phe Val Leu Asn Tyr Ser Lys Ala Met
            175                 180                 185 gag aac ctg ttc atc aac cgc ttc atg cac atg ttc cag tct tcc tgg        688
Glu Asn Leu Phe Ile Asn Arg Phe Met His Met Phe Gln Ser Ser Trp
        190                 195                 200 cac gac ttt gct gac ttt gag aaa atc ttc gtc aaa atc agc aac act        736
His Asp Phe Ala Asp Phe Glu Lys Ile Phe Val Lys Ile Ser Asn Thr
            205                 210                 215 ata tct gag cga gtc aag aac cac tgg cag gaa gac ctc atg ttt ggc        784
Ile Ser Glu Arg Val Lys Asn His Trp Gln Glu Asp Leu Met Phe Gly
        220                 225                 230 tac cag ttc ctg aat ggc tgc aac cca gta ctc atc aag cgc tgc aca        832
Tyr Gln Phe Leu Asn Gly Cys Asn Pro Val Leu Ile Lys Arg Cys Thr
235                 240                 245                 250 gcg ttg ccc ccg aag ctc cca gtg acc aca gag atg gtg gag tgc agc        880
Ala Leu Pro Pro Lys Leu Pro Val Thr Thr Glu Met Val Glu Cys Ser
            255                 260                 265 cta gag cgg cag ctc agt tta gaa cag gaa gta cag gaa ggg aac att        928
Leu Glu Arg Gln Leu Ser Leu Glu Gln Glu Val Gln Glu Gly Asn Ile
        270                 275                 280 ttc atc gtt gat tac gag cta ctg gat ggc atc gat gct aac aaa act        976
Phe Ile Val Asp Tyr Glu Leu Leu Asp Gly Ile Asp Ala Asn Lys Thr
            285                 290                 295 gac ccc tgt aca cac cag ttc ctg gct gcc ccc atc tgc ctg cta tat       1024
Asp Pro Cys Thr His Gln Phe Leu Ala Ala Pro Ile Cys Leu Leu Tyr
        300                 305                 310 aag aac cta gcc aac aag att gtt ccc att gcc atc cag ctc aac caa       1072
Lys Asn Leu Ala Asn Lys Ile Val Pro Ile Ala Ile Gln Leu Asn Gln
315                 320                 325                 330 acc cct gga gag agt aac cca atc ttc ctc cct acg gat tca aag tac       1120
Thr Pro Gly Glu Ser Asn Pro Ile Phe Leu Pro Thr Asp Ser Lys Tyr
            335                 340                 345 gac tgg ctt ttg gcc aaa atc tgg gtg cgt tcc agt gac ttc cac gtc       1168
Asp Trp Leu Leu Ala Lys Ile Trp Val Arg Ser Ser Asp Phe His Val
        350                 355                 360 cat caa acg atc acc cac ctt ctg cgc acg cat ctg gtg tct gag gtg       1216
His Gln Thr Ile Thr His Leu Leu Arg Thr His Leu Val Ser Glu Val
            365                 370                 375 ttt ggt atc gcc atg tac cgc cag ctg cct gct gtg cat ccc ctt ttc       1264
Phe Gly Ile Ala Met Tyr Arg Gln Leu Pro Ala Val His Pro Leu Phe
        380                 385                 390 aag ctg ctg gta gcc cat gtg agg ttc acc att gct atc aac act aag       1312
Lys Leu Leu Val Ala His Val Arg Phe Thr Ile Ala Ile Asn Thr Lys
395                 400                 405                 410 gcc cgg gaa cag ctt atc tgc gag tat ggc ctt ttt gac aag gcc aat       1360
Ala Arg Glu Gln Leu Ile Cys Glu Tyr Gly Leu Phe Asp Lys Ala Asn
            415                 420                 425
```

-continued

| | |
|---|---|
| gcc acc ggg ggt gga ggg cac gtg cag atg gtg cag agg gct gtc cag<br>Ala Thr Gly Gly Gly Gly His Val Gln Met Val Gln Arg Ala Val Gln<br>          430                    435                 440 | 1408 |
| gat ctg acc tat tcc tcc ctg tgt ttc ccg gag gcc atc aag gcc cgg<br>Asp Leu Thr Tyr Ser Ser Leu Cys Phe Pro Glu Ala Ile Lys Ala Arg<br>              445                 450                 455 | 1456 |
| ggc atg gac agc acg gaa gac atc ccc ttc tac ttc tat cgt gat gat<br>Gly Met Asp Ser Thr Glu Asp Ile Pro Phe Tyr Phe Tyr Arg Asp Asp<br>      460                 465                 470 | 1504 |
| gga ctg ctc gtg tgg gag gct atc cag tcg ttc aca atg gag gtg gtg<br>Gly Leu Leu Val Trp Glu Ala Ile Gln Ser Phe Thr Met Glu Val Val<br>475                 480                 485                 490 | 1552 |
| agc atc tac tat gag aac gac cag gtg gtg gag gag gac cag gaa ctg<br>Ser Ile Tyr Tyr Glu Asn Asp Gln Val Val Glu Glu Asp Gln Glu Leu<br>              495                 500                 505 | 1600 |
| cag gac ttc gtg aag gat gtt tac gtg tac ggc atg cgg ggc aaa aag<br>Gln Asp Phe Val Lys Asp Val Tyr Val Tyr Gly Met Arg Gly Lys Lys<br>      510                 515                 520 | 1648 |
| gcc tca ggt ttc ccc aag tcc atc aag agc agg gag aag ctg tcc gag<br>Ala Ser Gly Phe Pro Lys Ser Ile Lys Ser Arg Glu Lys Leu Ser Glu<br>          525                 530                 535 | 1696 |
| tac ctg acg gtg gtg atc ttc acg gcc tct gcc cag cat gca gct gta<br>Tyr Leu Thr Val Val Ile Phe Thr Ala Ser Ala Gln His Ala Ala Val<br>540                 545                 550 | 1744 |
| aac ttc ggc cag tat gac tgg tgc tcc tgg atc ccc aac gct cct cca<br>Asn Phe Gly Gln Tyr Asp Trp Cys Ser Trp Ile Pro Asn Ala Pro Pro<br>555                 560                 565                 570 | 1792 |
| act atg cgg gcc cca cca ccc acg gcc aag ggt gtg gtc acc atc gag<br>Thr Met Arg Ala Pro Pro Pro Thr Ala Lys Gly Val Val Thr Ile Glu<br>              575                 580                 585 | 1840 |
| cag atc gtg gat act cta cca gac cgt ggc cga tca tgt tgg cat cta<br>Gln Ile Val Asp Thr Leu Pro Asp Arg Gly Arg Ser Cys Trp His Leu<br>          590                 595                 600 | 1888 |
| ggt gca gtg tgg gcc ttg agc cag ttt caa gaa aat gag ctg ttt cta<br>Gly Ala Val Trp Ala Leu Ser Gln Phe Gln Glu Asn Glu Leu Phe Leu<br>          605                 610                 615 | 1936 |
| ggc atg tac cca gag gag cat ttc att gag aag cca gtg aag gaa gcc<br>Gly Met Tyr Pro Glu Glu His Phe Ile Glu Lys Pro Val Lys Glu Ala<br>      620                 625                 630 | 1984 |
| atg atc cga ttc cgc aag aac ctg gag gcc atc gtc agc gtg atc gcc<br>Met Ile Arg Phe Arg Lys Asn Leu Glu Ala Ile Val Ser Val Ile Ala<br>635                 640                 645                 650 | 2032 |
| gag cgc aat aag aac aaa aag ctc ccc tac tac tac ctg tca cca gac<br>Glu Arg Asn Lys Asn Lys Lys Leu Pro Tyr Tyr Tyr Leu Ser Pro Asp<br>              655                 660                 665 | 2080 |
| agg att ccc aac agt gta gcc atc taa<br>Arg Ile Pro Asn Ser Val Ala Ile *<br>          670 | 2107 |

What is claimed is:

1. A method for detecting a predisposition to atherosclerosis in a human, the method comprising:
   analyzing the genomic sequence of said human for the presence of predisposing 5-lipoxygenase (5-LO) alleles;
   identifying, on both chromosomes, said alleles comprising not more than 4 SP1/Egr-1 binding sites instead of the common 5 tandemly repeated Sp1/Egr-1 binding sites in the 5-lipoxygenase promoter;
   wherein the presence of said alleles is indicative that said human has a predisposition to atherosclerosis.

2. The method of claim 1, wherein said analyzing the genomic sequence comprises the steps of:
   amplifying a region of the 5-lipoxygenase promoter from isolated genomic DNA to provide an amplified fragment;
   detecting the presence of a polymorphic sequence in said amplified fragment.

3. The method of claim 2, wherein said detecting step comprises hybridization with a probe specific for the sequence of said polymorphism.

* * * * *

UNITED STATES PATENT AND TRADEMARK OFFICE
CERTIFICATE OF CORRECTION

| | | |
|---|---|---|
| PATENT NO. | : 7,241,571 B2 | Page 1 of 1 |
| APPLICATION NO. | : 10/741292 | |
| DATED | : July 10, 2007 | |
| INVENTOR(S) | : Margarete Mehrabian | |

It is certified that error appears in the above-identified patent and that said Letters Patent is hereby corrected as shown below:

Replace the paragraph in Column 1, lines 7-9 with the following paragraph:

--This invention was made with Government support of Grant Nos. HL42488, HL30568 and HL42481 awarded by the National Institutes of Health and was supported by a grant from the American Heart Association Grant-in-Aid 0355031Y. The Government has certain rights in this invention.--

Signed and Sealed this

Twenty-fourth Day of March, 2009

JOHN DOLL
*Acting Director of the United States Patent and Trademark Office*